US005663379A

United States Patent [19]

Karrer

[11] Patent Number: 5,663,379

[45] Date of Patent: Sep. 2, 1997

[54] SUBSTITUTED PHENYL ETHERS

[75] Inventor: Friedrich Karrer, Zofingen, Switzerland

[73] Assignee: Ciba-Geigy Corporation, Tarrytown, N.Y.

[21] Appl. No.: 366,128

[22] Filed: Dec. 29, 1994

[30] Foreign Application Priority Data

Dec. 30, 1993 [CH] Switzerland ............................ 3905/93

[51] Int. Cl.$^6$ ...................... C07D 317/00; C07D 307/77; A61K 31/335

[52] U.S. Cl. ............................................ 549/453; 549/456

[58] Field of Search ............................ 514/467; 549/450, 549/451, 453

[56] References Cited

U.S. PATENT DOCUMENTS

| | | | |
|---|---|---|---|
| 4,097,581 | 6/1978 | Faroog et al. | 424/278 |
| 4,590,282 | 5/1986 | Henrick | 549/453 |
| 4,971,981 | 11/1990 | Karrer | 514/336 |

FOREIGN PATENT DOCUMENTS

| | | |
|---|---|---|
| 0559612 | 9/1993 | European Pat. Off. . |

OTHER PUBLICATIONS

Chemical Abstracts Service CA 105: 97457, (citing US. 4590282 May 20, 1986).

*Primary Examiner*—Shean C. Wu
*Attorney, Agent, or Firm*—Marla J. Mathias; William A. Teoli, Jr.

[57] ABSTRACT

Compounds of the formula (I)

in which $R_1$, $R_2$, $R_3$, $R_4$, $R_5$ and $R_6$ are as defined in claim 1 can be used as agrochemical active ingredients and can be prepared in a manner known per se.

7 Claims, No Drawings

SUBSTITUTED PHENYL ETHERS

The invention relates to compounds of the formula

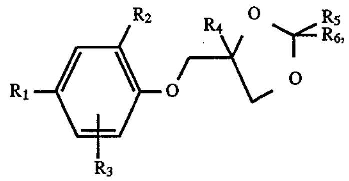

(I)

in which $R_1$ is substituted or unsubstituted $C_1$–$C_8$alkyl, substituted or unsubstituted $C_3$–$C_8$cycloalkyl, substituted or unsubstituted $C_2$–$C_8$alkenyl, substituted or unsubstituted $C_2$–$C_8$alkynyl, substituted or unsubstituted $C_1$–$C_8$alkoxy, substituted or unsubstituted $C_3$–$C_8$cycloalkoxy, substituted or unsubstituted $C_2$–$C_8$alkenyloxy, substituted or unsubstituted $C_2$–$C_8$alkynyloxy or substituted or unsubstituted $C_1$–$C_8$alkylthio;

$R_2$ is chlorine, bromine, methyl or monohalomethyl;

$R_3$ is H, halogen or methyl;

$R_4$ is H or methyl;

$R_5$ is H, $C_1$–$C_8$alkyl, $C_3$–$C_6$cycloalkyl, $C_2$–$C_5$alkenyl, $C_2$–$C_5$alkynyl, $C_1$–$C_3$alkoxy-$C_1$–$C_3$alkyl, $C_1$–$C_4$cyanoalkyl, $C_1$–$C_6$haloalkyl, $C_2$–$C_5$haloalkenyl, $C_2$–$C_3$haloalkynyl, $C_1$–$C_3$alkoxycarbonyl, trifluoromethylphenyl, benzyl or substituted benzyl, the substituents being selected from the group consisting of $C_1$–$C_3$alkyl, $C_1$–$C_3$alkoxy and halogen; and $R_6$ is H, $C_1$–$C_6$alkyl, $C_3$–$C_6$cycloalkyl, $C_2$–$C_5$alkenyl, $C_2$–$C_4$alkynyl, $C_1$–$C_4$alkoxy, phenyl, substituted phenyl, the substituents being selected from the group consisting of $C_1$–$C_3$alkyl, $C_1$–$C_3$alkoxy, $C_1$–$C_3$haloalkyl, $C_1$–$C_3$haloalkoxy, $C_1$–$C_3$alkylenedioxy and halogen; pyridyl, halopyridyl, furyl, thienyl, or $R_5$ and $R_6$ together are straight-chain $C_3$–$C_5$alkylene;

to a process for the preparation and to the use of these compounds, to pesticides whose active ingredient is selected from amongst these compounds, and to a process for the preparation and to the use of these compositions and intermediates for the preparation of the compounds of the formula I.

Certain dioxolane derivatives are proposed in the literature as insecticidally acting active ingredients in pesticides. However, the biological characteristics of these known compounds are not entirely satisfactory in the field of pest control, which is why there is a demand for providing other compounds having pesticidal characteristics, in particular for controlling insects and representatives of the order Acarina, this object being achieved according to the invention by providing the present compounds I.

Unless otherwise defined, the general terms used hereinabove and hereinbelow are defined as follows.

Unless otherwise defined, carbon-containing groups and compounds have in each case 1 up to and including 8, preferably 1 up to and including 6, in particular 1 or 2, carbon atoms.

Alkyl-as a group per se and as structural element of other groups and compounds, such as phenylalkyl, alkylphenyl, haloalkyl, alkoxy, alkoxyalkyl, alkoxyalkoxy, haloalkoxy, alkylthio, alkylthioalkyl, alkylthioalkoxy and alkylthioalkylthio, - is, in each case with due consideration of the number of carbon atoms which the relevant group or compound has in each individual case, either straight-chain, i.e. methyl, ethyl, propyl, butyl, pentyl, hexyl, heptyl or octyl, or branched, for example isopropyl, isobutyl, sec-butyl, tert-butyl, isopentyl, neopentyl, isohexyl, isoheptyl or isooctyl. Examples of alkoxyalkyl are methoxymethyl, ethoxymethyl, ethoxyethyl or 2-methoxybutyl; examples of alkoxyalkoxy are methoxyethoxy or ethoxyethoxy; examples of alkylthioalkyl are ethylthiomethyl or isobutylthiomethyl; examples of alkylthioalkoxy are ethylthioethoxy or i-propylthioethoxy; examples of alkylthioalkylthio are methylthioethylthio or i-propylthioethylthio.

Alkenyl, alkenyloxy, alkenyloxyalkyl, haloalkenyl, haloalkenyloxy, haloalkenyloxyalkyl, alkynyl, alkynyloxy, alkynyloxyalkyl, haloalkynyl, haloalkynyloxy and haloalkynyloxyalkyl are straight-chain or branched and have in each case two or preferably one unsaturated carbon-carbon bond (s). Examples of alkenyloxyalkyl are allyloxymethyl or 2-buten-1-yloxymethyl; examples of alkynyloxyalkyl are 2-propyn-1-yloxymethyl or 2-pentyn-1-yloxymethyl.

Cycloalkyl is cyclopropyl, cyclobutyl, cyclopentyl, cyclohexyl, cycloheptyl or cyclooctyl, preferably cyclopropyl or cyclohexyl.

$C_1$–$C_3$Alkylenedioxy is —O—$CH_2$—O—, —O—$CH_2$—$CH_2$—O— or —O—$CH_2$—$CH_2$—$CH_2$—O—, preferably —O—$CH_2$—O—.

Straight-chain $C_3$–$C_5$alkylene is trimethylene, tetramethylene or pentamethylene.

$C_1$–$C_4$Cyanoalkyl is cyanomethyl, cyanoethyl, cyanopropyl or cyanoisopropyl, especially cyanomethyl.

Halogen-as a group per se and as structural element of other groups and compounds, such as of haloalkyl and haloalkoxy, - is fluorine, chlorine, bromine or iodine, in particular fluorine, chlorine or bromine, especially chlorine or bromine.

Halogen-substituted carbon-containing groups and compounds, such as haloalkyl, haloalkylthio, haloalkoxy, haloalkenyl, haloalkenyloxy, haloalkenyloxyalkyl, haloalkynyl, haloalkynyloxy, haloalkynyloxyalkyl and haloallyloxy, can be partially halogenated or perhalogenated, it being possible for the halogen substituents to be identical or different in the case of polyhalogenation. Examples of haloalkyl-as a group per se and as structural element of other groups and compounds, such as of haloalkoxy,-these are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which are mono- to heptasubstituted by fluorine, chlorine and/or bromine, such as $CH_2CHBrCH_2Br$, $CF_2CHFCF_3$, $CH_2CF_2CF_3$, $CF_2CF_2CF_3$ or $CH(CF_3)_2$; and butyl which is mono- to nonasubstituted by fluorine, chlorine and/or bromine, or one of its isomers, such as $CF(CF_3)CHFCF_3$, $CF_2(CF_2)_2CF_3$ or $CH_2(CF_2)_2CF_3$. Examples of haloalkenyl are 2,2-difluoroethenyl, 2,2-dichloroethenyl, 3-chloro-2-allyl, 3,3-dichloro-2-allyl and 2,3-dibromo-2-allyl. Examples of haloalkynyl are 3-chloro-2-propynyl, 1,3-dichloro-2-propynyl and 1,3-dibromo-2-propynyl.

Preferred embodiments within the scope of the invention are:

(1) A compound of the formula I in which $R_1$ is $C_1$–$C_8$alkyl, $C_3$–$C_8$cycloalkyl, $C_2$–$C_8$alkenyl, $C_2$–$C_8$alkynyl, $C_1$–$C_8$alkoxy, $C_3$–$C_8$cycloalkoxy, $C_2$–$C_8$alkoxy-$C_1$–$C_4$alkyl, $C_1$–$C_8$alkoxy-$C_2$–$C_4$alkoxy-$C_1$–$C_4$alkyl, $C_1$–$C_8$alkoxy-$C_2$–$C_4$alkoxy, $C_4$–$C_8$cycloalkoxy-$C_1$–$C_3$alkyl, $C_3$–$C_8$alkenyloxy, $C_3$–$C_8$alkenyloxy-$C_1$–$C_3$alkyl, $C_3$–$C_8$alkynyloxy, $C_3$–$C_8$alkynyloxy-$C_1$–$C_3$alkyl, $C_3$–$C_8$haloalkyl, $C_3$–$C_8$haloalkenyl, $C_3$–$C_8$haloalkynyl, $C_3$–$C_8$haloalkoxy, $C_3$–$C_8$haloalkoxy, $C_1$–$C_3$alkyl, $C_3$–$C_8$haloalkenyloxy, $C_3$–$C_8$haloalkenyloxy-$C_1$–$C_3$alkyl, $C_3$–$C_8$haloalkynyloxy, $C_3$–$C_8$haloalkynyloxy-$C_1$–$C_3$alkyl, $C_3$–$C_8$alkylthio, $C_3$–$C_8$alkylthio-$C_1$–$C_3$alkyl, $C_2$–$C_8$alkylthio-$C_2$–$C_3$alkoxy, $C_2$–$C_8$alkylthio-$C_2$–$C_3$alkoxy, $C_1$–$C_4$alkyl, $C_2$–$C_8$alkylthio-$C_2$–$C_3$alkylthio, $C_2$–$C_8$alkylthio-$C_2$–$C_3$alkylthio-$C_1$–$C_4$alkyl, $C_2$–$C_8$alkoxy-$C_2$–$C_3$alkylthio or $C_2$–$C_8$alkoxy-$C_2$–$C_3$alkylthio-$C_1$–$C_4$alkyl; especially $C_3$–$C_6$alkyl, $C_3$–$C_6$cycloalkyl, $C_3$–$C_6$alkenyl, $C_3$–$C_6$alkynyl, $C_3$–$C_8$alkoxy, $C_3$–$C_6$cycloalkoxy, $C_2$–$C_6$alkoxy-$C_1$–$C_4$alkyl, $C_1$–$C_6$alkoxy-$C_2$–$C_4$alkoxy, $C_4$–$C_6$cycloalkoxy-$C_1$–$C_3$alkyl, $C_3$–$C_6$alkenyloxy, $C_3$–$C_6$alkenyloxy-$C_1$–$C_3$alkyl, $C_3$–$C_6$alkynyloxy, $C_3$–$C_6$alkynyloxy-$C_1$–$C_3$alkyl, $C_3$–$C_6$haloalkyl, $C_3$–$C_6$haloalkenyl, $C_3$–$C_6$haloalkynyl, $C_3$–$C_6$haloalkoxy, $C_3$–$C_6$haloalkoxy-$C_1$–$C_3$alkyl, $C_3$–$C_6$haloalkenyloxy, $C_3$–$C_6$haloalkenyloxy-$C_1$–$C_3$alkyl, $C_3$–$C_6$haloalkynyloxy, $C_3$–$C_6$haloalkynloxy-$C_1$–$C_3$alkyl, $C_3$–$C_6$alkylthio, $C_3$–$C_6$alkylthio-$C_1$–$C_3$alkyl, $C_2$–$C_6$alkylthio-$C_2$–$C_3$alkoxy or $C_2$–$C_6$alkylthio-$C_2$–$C_3$alkylthio;

in particular $C_4$–$C_6$alkyl, $C_4$–$C_6$cycloalkyl, $C_3$–$C_6$alkenyl, $C_3$–$C_5$alkynyl, $C_4$–$C_8$alkoxy, $C_5$–$C_6$cycloalkoxy, $C_2$–$C_4$alkoxy-$C_1$–$C_4$alkyl, $C_1$–$C_3$alkoxy-$C_2$–$C_4$alkoxy, $C_5$–$C_6$cycloalkoxy-$C_1$–$C_2$alkyl, $C_4$–$C_6$alkenyloxy, $C_3$–$C_5$alkenyloxy-$C_1$–$C_2$alkyl, $C_3$–$C_5$alkynyloxy, $C_3$–$C_5$alkynyloxy-$C_1$–$C_2$alkyl, $C_3$–$C_5$haloalkyl, $C_3$–$C_5$haloalkenyl, $C_3$–$C_5$haloalkynyl, $C_3$–$C_5$haloalkoxy, $C_3$–$C_5$haloalkoxy-$C_1$–$C_2$alkyl, $C_3$–$C_4$haloalkenyloxy, $C_3$–$C_4$haloalkenyloxy-$C_1$–$C_2$alkyl, $C_3$–$C_4$haloalkynyloxy, $C_3$–$C_4$haloalkynyloxy-$C_1$–$C_2$alkyl, $C_3$–$C_5$alkylthio, $C_3$–$C_5$alkylthio-$C_1$–$C_2$alkyl, $C_2$–$C_4$alkylthio-$C_2$–$C_3$alkoxy or $C_2$–$C_4$alkylthio-$C_2$–$C_3$alkylthio;

very particularly $C_4$–$C_6$alkyl, cyclohexyl, $C_4$–$C_5$alkynyl, $C_4$–$C_5$alkoxy, $C_5$–$C_6$cycloalkoxy, $C_2$–$C_4$alkoxy-$C_1$–$C_4$alkyl, $C_1$–$C_2$alkoxyethoxy, $C_5$–$C_6$cycloalkoxymethyl, $C_4$–$C_6$alkenyloxy, $C_3$–$C_5$alkenyloxymethyl, $C_3$–$C_5$alkynyloxy, $C_3$–$C_4$haloalkoxy, $C_3$haloalkenyloxy, $C_3$haloalkenyloxymethyl, $C_3$haloalkynyloxy, $C_3$haloalkynyloxymethyl, $C_4$alkylthio, $C_4$alkylthiomethyl, $C_2$–$C_3$alkylthioethoxy or $C_2$–$C_3$alkylthioethylthio;

(2) a compound of the formula I in which $R_2$ is chlorine, bromine, methyl or chloromethyl; especially chlorine, bromine or methyl; in particular chlorine or bromine;

(3) a compound of the formula I in which $R_3$ is H, bromine or methyl; especially H or bromine; in particular H;

(4) a compound of the formula I in which $R_4$ is H;

(5) a compound of the formula I in which $R_5$ is H, $C_1$–$C_8$alkyl, $C_3$–$C_6$cycloalkyl, $C_2$–$C_4$alkenyl, $C_2$–$C_3$alkynyl, $C_1$–$C_3$alkoxy-$C_1$–$C_3$alkyl, $C_2$–$C_4$cyanoalkyl, $C_2$–$C_6$haloalkyl, $C_2$–$C_5$haloalkenyl, $C_2$–$C_3$haloalkynyl, $C_1$–$C_3$alkoxycarbonyl, trifluoromethylphenyl, benzyl or substituted benzyl, the substituents being selected from the group consisting of $C_1$–$C_3$alkyl, $C_1$–$C_3$alkoxy and chlorine;

especially H, $C_1$–$C_8$alkyl, $C_3$–$C_6$cycloalkyl, $C_2$–$C_4$alkenyl, $C_2$–$C_3$alkynyl, methoxyethyl, cyanomethyl, haloethyl, halovinyl, haloacetylenyl, trifluoromethylphenyl, benzyl or substituted benzyl, the substituents being selected from the group consisting of methyl, methoxy and chlorine;

in particular H, $C_1$–$C_8$alkyl, cyclopropyl, $C_2$–$C_4$alkenyl, $C_2$–$C_3$alkynyl, methoxyethyl, cyanomethyl, fluoroethyl, chloroethyl, fluorovinyl, chlorovinyl, bromovinyl, iodacetylenyl, trifluoromethylphenyl, benzyl, tolyl, anisyl or chlorophenyl;

(6) a compound of the formula I in which $R_6$ is H, $C_1$–$C_6$alkyl, $C_3$–$C_6$cycloalkyl, $C_2$–$C_5$alkenyl, $C_2$–$C_4$alkynyl, $C_1$–$C_4$alkoxy, phenyl, substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_3$alkylenedioxy and halogen; pyridyl, halopyridyl, furyl or $R_5$ and $R_6$ together are $C_3$–$C_5$alkylene; especially H, $C_1$–$C_3$alkyl, $C_3$–$C_6$cycloalkyl, $C_2$–$C_3$alkenyl, $C_2$–$C_3$alkynyl, $C_1$–$C_3$alkoxy, phenyl, substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_2$alkylenedioxy and halogen; pyridyl, halopyridyl, furyl, or $R_5$ and $R_6$ together are $C_3$–$C_5$alkylene; in particular H, $C_1$–$C_3$alkyl, $C_3$–$C_6$cycloalkyl, vinyl, acetylenyl, $C_1$–$C_2$alkoxy, phenyl, 4-tolyl, 4-ethylphenyl, anisyl, trifluoromethylphenyl, methylenedioxyphenyl, fluorophenyl, difluorophenyl, chlorophenyl, dichlorophenyl, pyridyl, chloropyridyl, furyl, or $R_5$ and $R_6$ together are $C_3$–$C_5$alkylene;

(7) a compound of the formula I in which $R_1$ is $C_3$–$C_6$alkyl, $C_3$–$C_6$cycloalkyl, $C_3$–$C_6$alkenyl, $C_3$–$C_6$alkynyl, $C_3$–$C_8$alkoxy, $C_3$–$C_6$cycloalkoxy, $C_2$–$C_6$alkoxy-$C_1$–$C_4$alkyl, $C_1$–$C_6$alkoxy-$C_2$–$C_4$alkoxy, $C_4$–$C_6$cycloalkoxy-$C_1$–$C_3$alkyl, $C_3$–$C_6$alkenyloxy, $C_3$–$C_6$alkenyloxy-$C_1$–$C_3$alkyl, $C_3$–$C_6$alkynyloxy, $C_3$–$C_6$alkynyloxy-$C_1$–$C_3$alkyl, $C_3$–$C_6$haloalkyl, $C_3$–$C_6$haloalkenyl, $C_3$–$C_6$haloalkynyl, $C_3$–$C_6$haloalkoxy, $C_3$–$C_6$haloalkoxy-$C_1$–$C_3$alkyl, $C_3$–$C_6$haloalkenyloxy, $C_3$–$C_6$haloalkenyloxy-$C_1$–$C_3$alkyl, $C_3$–$C_6$haloalkynyloxy, $C_3$–$C_6$haloalkynyloxy-$C_1$–$C_3$alkyl, $C_3$–$C_6$alkylthio, $C_3$–$C_6$alkylthio-$C_1$–$C_3$alkyl, $C_2$–$C_6$alkylthio-$C_2$–$C_3$alkoxy or $C_2$–$C_6$alkylthio-$C_2$–$C_3$alkylthio;

$R_2$ is fluorine, chlorine, bromine or methyl;

$R_5$ is H, $C_1$–$C_8$alkyl, $C_3$–$C_6$cycloalkyl, $C_2$–$C_4$alkenyl, $C_2$–$C_3$alkynyl, $C_1$–$C_3$alkoxy-$C_1$–$C_3$alkyl, $C_2$–$C_4$cyanoalkyl, $C_2$–$C_6$haloalkyl, $C_2$–$C_5$haloalkenyl, $C_2$–$C_3$haloalkynyl, $C_1$–$C_3$alkoxycarbonyl, trifluoromethylphenyl, benzyl or substituted benzyl, the substituents being selected from the group consisting of $C_1$–$C_3$alkyl, $C_1$–$C_3$alkoxy and chlorine; and $R_6$ is H, $C_1$–$C_6$alkyl, $C_3$–$C_6$cycloalkyl, $C_2$–$C_5$alkenyl, $C_2$–$C_4$alkynyl, $C_1$–$C_4$alkoxy, phenyl, substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_3$alkylenedioxy and halogen; pyridyl, halopyridyl, furyl, or $R_5$ and $R_6$ together are $C_3$–$C_5$alkylene;

(8) a compound of the formula I in which $R_1$ is $C_4$–$C_6$alkyl, $C_4$–$C_6$cycloalkyl, $C_3$–$C_6$alkenyl, $C_3$–$C_5$alkynyl, $C_4$–$C_8$alkoxy, $C_5$–$C_6$cycloalkoxy, $C_2$–$C_4$alkoxy-$C_1$–$C_4$alkyl, $C_1$–$C_3$alkoxy-$C_2$–$C_4$alkoxy, $C_5$–$C_6$cycloalkoxy-$C_1$–$C_2$alkyl, $C_4$–$C_6$alkenyoxy, $C_3$–$C_5$alkenyloxy-$C_1$–$C_2$alkyl, $C_3$–$C_5$alkynyoxy, $C_3$–$C_5$alkynyoxy-$C_1$–$C_2$alkyl, $C_3$–$C_5$haloalkyl, $C_3$–$C_5$haloalkenyl, $C_3$–$C_5$haloalkynyl, $C_3$–$C_5$haloalkoxy, $C_3$–$C_5$haloalkoxy-$C_1$–$C_2$alkyl, $C_3$–$C_4$haloalkenyloxy, $C_3$–$C_4$haloalkenyloxy-$C_1$–$C_2$alkyl, $C_3$–$C_4$haloalkynyloxy, $C_3$–$C_4$haloalkynyloxy-$C_1$–$C_2$alkyl, $C_3$–$C_5$alkylthio, $C_3$–$C_5$alkylthio-$C_1$–$C_2$alkyl, $C_2$–$C_4$alkylthio-$C_2$–$C_3$alkoxy or $C_2$–$C_4$alkylthio-$C_2$–$C_3$alkylthio;

$R_2$ is fluorine, chlorine, bromine or methyl;

$R_5$ is H, $C_1$–$C_8$alkyl, $C_3$–$C_6$cycloalkyl, $C_2$–$C_4$alkenyl, $C_2$–$C_3$alkynyl, $C_1$–$C_3$alkoxy-$C_1$–$C_3$alkyl, $C_2$–$C_4$cyanoalkyl, $C_2$–$C_6$haloalkyl, $C_2$–$C_5$haloalkenyl, $C_2$–$C_3$haloalkynyl, $C_1$–$C_3$alkoxycarbonyl, trifluoromethylphenyl, benzyl or substituted benzyl, the substituents being selected from the group consisting of $C_1$–$C_3$alkyl, $C_1$–$C_3$alkoxy and chlorine; and $R_6$ is H, $C_1$–$C_6$alkyl, $C_3$–$C_6$cycloalkyl, $C_2$–$C_5$alkenyl, $C_2$–$C_4$alkynyl, $C_1$–$C_4$alkoxy, phenyl, substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_3$alkylenedioxy and halogen; pyridyl, halopyridyl, furyl, or $R_5$ and $R_6$ together are $C_3$–$C_6$alkylene;

(9) a compound of the formula I in which $R_1$ is $C_4$–$C_6$alkyl, $C_4$–$C_6$cycloalkyl, $C_3$–$C_6$alkenyl, $C_3$–$C_5$alkynyl, $C_4$–$C_8$alkoxy, $C_5$–$C_6$cycloalkoxy, $C_2$–$C_4$alkoxy-$C_1$–$C_4$alkyl, $C_1$–$C_3$alkoxy-$C_2$–$C_4$alkoxy, $C_5$–$C_6$cycloalkoxy-$C_1$–$C_2$alkyl, $C_4$–$C_6$alkenyoxy, $C_3$–$C_5$alkenyoxy-$C_1$–$C_2$alkyl, $C_3$–$C_5$alkynyloxy, $C_3$–$C_5$alkynyloxy-$C_1$–$C_2$alkyl, $C_3$–$C_5$haloalkyl, $C_3$–$C_5$haloalkenyl, $C_3$–$C_5$haloalkynyl, $C_3$–$C_5$haloalkoxy, $C_3$–$C_5$haloalkoxy-$C_1$–$C_2$alkyl, $C_3$–$C_4$haloalkenyloxy, $C_3$–$C_4$haloalkenyloxy-$C_1$–$C_2$alkyl, $C_3$–$C_4$haloalkynyloxy, $C_3$–$C_4$haloalkynyloxy-$C_1$–$C_2$alkyl, $C_3$–$C_5$alkylthio, $C_3$–$C_5$alkylthio-$C_1$–$C_2$alkyl, $C_2$–$C_4$alkylthio-$C_2$–$C_3$alkoxy or $C_2$–$C_4$alkylthio-$C_2$–$C_3$alkylthio;

$R_2$ is chlorine, bromine or methyl;

$R_5$ is H, $C_1$–$C_8$alkyl, $C_3$–$C_6$cycloalkyl, $C_2$–$C_4$alkenyl, $C_2$–$C_3$alkynyl, $C_1$–$C_3$alkoxy-$C_1$–$C_3$alkyl, $C_2$–$C_4$cyanoalkyl, $C_2$–$C_6$haloalkyl, $C_2$–$C_5$haloalkenyl, $C_2$–$C_3$haloalkynyl, $C_1$–$C_3$alkoxycarbonyl, trifluoromethylphenyl, benzyl or substituted benzyl, the substituents being selected from the group consisting of $C_1$–$C_3$alkyl, $C_1$–$C_3$alkoxy and chlorine; and $R_6$ is H, $C_1$–$C_6$alkyl, $C_3$–$C_6$cycloalkyl, $C_2$–$C_5$alkenyl, $C_2$–$C_4$alkynyl, $C_1$–$C_4$alkoxy, phenyl, substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_3$alkylenedioxy and halogen; pyridyl, halopyridyl, furyl, or $R_5$ and $R_6$ together are $C_3$–$C_5$alkylene;

(10) a compound of the formula I in which $R_1$ is $C_4$–$C_6$alkyl, $C_4$–$C_6$cycloalkyl, $C_3$–$C_6$alkenyl, $C_3$–$C_5$alkynyl, $C_4$–$C_8$alkoxy, $C_5$–$C_6$cycloalkoxy, $C_2$–$C_4$alkoxy-$C_1$–$C_4$alkyl, $C_1$–$C_3$alkoxy-$C_2$–$C_4$alkoxy, $C_5$–$C_6$cycloalkoxy-$C_1$–$C_2$alkyl, $C_4$–$C_6$alkenyloxy, $C_3$–$C_5$alkenyloxy-$C_1$–$C_2$alkyl, $C_3$–$C_5$alkynyloxy, $C_3$–$C_5$alkynyloxy-$C_1$–$C_2$alkyl, $C_3$–$C_5$haloalkyl, $C_3$–$C_5$haloalkenyl, $C_3$–$C_5$haloalkynyl, $C_3$–$C_5$haloalkoxy, $C_3$–$C_5$haloalkoxy-$C_1$–$C_2$alkyl, $C_3$–$C_4$haloalkenyloxy, $C_3$–$C_4$haloalkenyloxy-$C_1$–$C_2$alkyl, $C_3$–$C_4$haloalkynyloxy, $C_3$–$C_4$haloalkynyloxy-$C_1$–$C_2$alkyl, $C_3$–$C_5$alkylthio, $C_3$–$C_5$alkylthio-$C_1$–$C_2$alkyl, $C_2$–$C_4$alkylthio-$C_2$–$C_3$alkoxy or $C_2$–$C_4$alkylthio-$C_2$–$C_3$alkylthio;

$R_2$ is chlorine, bromine or methyl;

$R_5$ is H, $C_1$–$C_8$alkyl, $C_3$–$C_6$cycloalkyl, $C_2$–$C_4$alkenyl, $C_2$–$C_3$alkynyl, methoxyethyl, cyanomethyl, haloethyl, halovinyl, haloacetylenyl, trifluoromethylphenyl, benzyl or substituted benzyl, the substituents being selected from the group consisting of methyl, methoxy and chlorine; and $R_6$ is H, $C_1$–$C_6$alkyl, $C_3$–$C_6$cycloalkyl, $C_2$–$C_5$alkenyl, $C_2$–$C_4$alkynyl, $C_1$–$C_4$alkoxy, phenyl, substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_3$alkylenedioxy and halogen; pyridyl, halopyridyl, furyl, or $R_5$ and $R_6$ together are $C_3$–$C_5$alkylene;

(11) a compound of the formula I in which $R_1$ is $C_4$–$C_6$alkyl, $C_4$–$C_6$cycloalkyl, $C_3$–$C_6$alkenyl, $C_3$–$C_5$alkynyl, $C_4$–$C_8$alkoxy, $C_5$–$C_6$cycloalkoxy, $C_2$–$C_4$alkoxy-$C_1$–$C_4$alkyl, $C_1$–$C_3$alkoxy-$C_2$–$C_4$alkoxy, $C_5$–$C_6$cycloalkoxy-$C_1$–$C_2$alkyl, $C_4$–$C_6$alkenyloxy, $C_3$–$C_5$alkenyloxy-$C_1$–$C_2$alkyl, $C_3$–$C_5$alkynyloxy, $C_3$–$C_5$alkynyloxy-$C_1$–$C_2$alkyl, $C_3$–$C_5$haloalkyl, $C_3$–$C_5$haloalkenyl, $C_3$–$C_5$haloalkynyl, $C_3$–$C_5$haloalkoxy, $C_3$–$C_5$haloalkoxy-$C_1$–$C_2$alkyl, $C_3$–$C_4$haloalkenyloxy, $C_3$–$C_4$haloalkenyloxy-$C_1$–$C_2$alkyl, $C_3$–$C_4$haloalkynyloxy, $C_3$–$C_4$haloalkynyloxy-$C_1$–$C_2$alkyl, $C_3$–$C_5$alkylthio, $C_3$–$C_5$alkylthio-$C_1$–$C_2$alkyl, $C_2$–$C_4$alkylthio-$C_2$–$C_3$alkoxy or $C_2$–$C_4$alkylthio-$C_2$–$C_3$alkylthio;

$R_2$ is chlorine, bromine or methyl;

$R_5$ is H, $C_1$–$C_8$alkyl, $C_3$–$C_6$cycloalkyl, $C_2$–$C_4$alkenyl, $C_2$–$C_3$alkynyl, methoxyethyl, cyanomethyl, haloethyl, halovinyl, haloacetylenyl, trifluoromethylphenyl, benzyl or substituted benzyl, the substituents being selected from the group consisting of methyl, methoxy and chlorine; and $R_6$ is H, $C_1$–$C_3$alkyl, $C_3$–$C_6$cycloalkyl, $C_2$–$C_3$alkenyl, $C_2$–$C_3$alkynyl, $C_1$–$C_3$alkoxy, phenyl substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_2$alkylenedioxy and halogen; pyridyl, halopyridyl, furyl, or $R_5$ and $R_6$ together are $C_3$–$C_5$alkylene;

(12) a compound of the formula I in which $R_1$ is $C_4$–$C_6$alkyl, cyclohexyl, $C_4$–$C_5$alkynyl, $C_4$–$C_5$alkoxy, $C_5$–$C_6$cycloalkoxy, $C_2$–$C_4$alkoxy-$C_1$–$C_4$alkyl, $C_1$–$C_2$alkoxyethoxy, $C_5$–$C_6$cycloalkoxymethyl, $C_4$–$C_6$alkenyloxy, $C_3$–$C_5$alkenyloxymethyl, $C_3$–$C_5$alkynyloxy, $C_3$–$C_4$haloalkoxy, $C_3$–$C_4$haloalkenyloxy, $C_3$–$C_4$haloalkenyloxymethyl, $C_3$–$C_4$haloalkynyloxy, $C_3$–$C_4$haloalkynyloxymethyl, $C_3$–$C_4$alkylthio, $C_3$–$C_4$alkylthiomethyl, $C_2$–$C_3$alkylthioethoxy or $C_2$–$C_3$alkylthioethylthio;

$R_2$ is chlorine, bromine or methyl;

$R_5$ is H, $C_1$–$C_8$alkyl, $C_3$–$C_6$cycloalkyl, $C_2$–$C_4$alkenyl, $C_2$–$C_3$alkynyl, methoxyethyl, cyanomethyl, haloethyl, halovinyl, haloacetylenyl, trifluoromethylphenyl, benzyl or substituted benzyl, the substituents being selected from the group consisting of methyl, methoxy and chlorine; and $R_6$ is H, $C_1$–$C_3$alkyl, $C_3$–$C_6$cycloalkyl, $C_2$–$C_3$alkenyl, $C_2$–$C_3$alkynyl, $C_1$–$C_3$alkoxy, phenyl, substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_2$alkylenedioxy and halogen; pyridyl, halopyridyl, furyl, or $R_5$ and $R_6$ together are $C_3$–$C_5$alkylene;

(13) a compound of the formula I in which $R_1$ is $C_4$–$C_6$alkyl, cyclohexyl, $C_4$–$C_5$alkynyl, $C_4$–$C_5$alkoxy, $C_5$–$C_6$cycloalkoxy, $C_2$–$C_4$alkoxy-$C_1$–$C_4$alkyl, $C_1$–$C_2$alkoxyethoxy, $C_5$–$C_6$cycloalkoxymethyl, $C_4$–$C_6$alkenyloxy, $C_3$–$C_5$alkenyloxymethyl, $C_3$–$C_5$alkynyloxy, $C_3$–$C_4$haloalkoxy, $C_3$–$C_4$haloalkenyloxy, $C_3$–$C_4$haloalkenyloxymethyl, $C_3$–$C_4$haloalkynyloxy, $C_3$–$C_4$haloalkynyloxymethyl, $C_3$–$C_4$alkylthio, $C_3$–$C_4$alkylthiomethyl, $C_2$–$C_3$alkylthioethoxy or $C_2$–$C_3$alkylthioethylthio;

$R_2$ is chlorine, bromine or methyl;

$R_5$ is H, $C_1$–$C_8$alkyl, cyclopropyl, $C_2$–$C_4$alkenyl, $C_2$–$C_3$alkynyl, methoxyethyl, cyanomethyl, fluoroethyl, chloroethyl, fluorovinyl, chlorovinyl, bromovinyl, iodacetylenyl, trifluoromethylphenyl, benzyl, tolyl, anisyl or chlorophenyl; and $R_6$ is H, $C_1$–$C_3$alkyl, $C_3$–$C_6$cycloalkyl, $C_2$–$C_3$alkenyl, $C_2$–$C_3$alkynyl, $C_1$–$C_3$alkoxy, phenyl, substituted phenyl, the substituents being selected from the group consisting of $C_1$–$C_2$alkyl, $C_1$–$C_2$alkoxy, $C_1$–$C_2$haloalkyl, $C_1$–$C_2$haloalkoxy, $C_1$–$C_2$alkylenedioxy and halogen; pyridyl, halopyridyl, furyl, or $R_5$ and $R_6$ together are $C_3$–$C_5$alkylene;

(14) a compound of the formula I in which $R_1$ is $C_4$–$C_6$alkyl, cyclohexyl, $C_4$–$C_5$alkynyl, $C_4$–$C_5$alkoxy, $C_5$–$C_6$cycloalkoxy, $C_2$–$C_4$alkoxy-$C_1$–$C_4$alkyl, $C_1$–$C_2$alkoxyethoxy, $C_5$–$C_6$cycloalkoxymethyl, $C_4$–$C_6$alkenyloxy, $C_3$–$C_5$alkenyloxymethyl, $C_3$–$C_5$alkynyloxy, $C_3$–$C_4$haloalkoxy, $C_3$–$C_4$haloalkenyloxy, $C_3$–$C_4$haloalkenyloxymethyl, $C_3$–$C_4$haloalkynyloxy, $C_3$–$C_4$haloalkynyloxymethyl, $C_3$–$C_4$alkylthio, $C_3$–$C_4$alkylthiomethyl, $C_2$–$C_3$alkylthioethoxy or $C_2$–$C_3$alkylthioethylthio;

$R_2$ is chlorine, bromine or methyl;

$R_5$ is H, $C_1$–$C_8$alkyl, cyclopropyl, $C_2$–$C_4$alkenyl, $C_2$–$C_3$alkynyl, methoxyethyl, cyanomethyl, fluoroethyl, chloroethyl, fluorovinyl, chlorovinyl, bromovinyl, iodacetylenyl, trifluoromethylphenyl, benzyl, tolyl, anisyl or chlorophenyl; and $R_6$ is H, $C_1$–$C_3$alkyl, $C_3$–$C_6$cycloalkyl, vinyl, acetylenyl, $C_1$–$C_2$alkoxy, phenyl, 4-tolyl, 4-ethylphenyl, anisyl, trifluoromethylphenyl, methylenedioxyphenyl, fluorophenyl, difluorophenyl, chlorophenyl, dichlorophenyl, pyridyl, chloropyridyl, furyl, or $R_5$ and $R_6$ together are $C_3$–$C_5$alkylene.

Compounds of the formula I which are particularly preferred within the scope of the invention are those mentioned in Examples H4, H8 and H11.

Compounds of the formula I which are very particularly preferred within the scope of the invention are those in which $R_1$ is sec-butoxy or isobutoxy, $R_2$ is chlorine or bromine, $R_3$ is H or bromine, $R_4$ and $R_6$ are H, and $R_5$ is ethyl or propyl.

The invention also provides a process for the preparation of the compounds of the formula I, which comprises, for example, a) reacting a compound of the formula

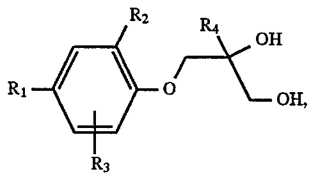

(II)

which is known or can be prepared in analogy to corresponding known compounds and in which $R_1$, $R_2$, $R_3$ and $R_4$ are as defined for formula I, in free form or in salt form, with a compound of the formula $R_5COR_6$ (III), which is known or can be prepared in analogy to corresponding known compounds and in which $R_5$ and $R_6$ are as defined for formula I, or with a compound of the formula

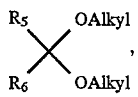

(IV) , which is known or can be prepared in analogy to corresponding known compounds and in which $R_5$ and $R_6$ are as defined for formula I and alkyl is methyl or ethyl, if appropriate in the presence of an acid catalyst or a dehydrating agent, or b) reacting a compound of the formula

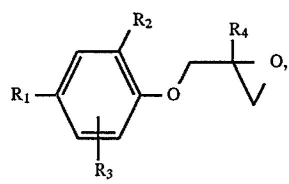

(V)

which is known or can be prepared in analogy to corresponding known compounds and in which $R_1$, $R_2$, $R_3$ and $R_4$ are as defined for formula I, with a compound of the formula III, if appropriate in the presence of an acid catalyst or a dehydrating agent, or c) reacting a compound of the formula

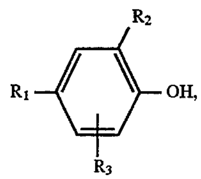

(VI)

which is known or can be prepared in analogy to corresponding known compounds and in which $R_1$, $R_2$ and $R_3$ are as defined for formula I, with a compound of the formula

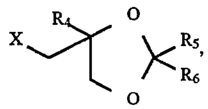

(VII)

which is known or can be prepared in analogy to corresponding known compounds and in which $R_4$, $R_5$ and $R_6$ are as defined for formula I and X is a leaving group, if appropriate in the presence of a base or a dehydrating agent, and/or, if desired, converting a compound of the formula I which can be obtained in accordance with the process or by a different route into a different compound of the formula I, and/or separating an isomer mixture which can be obtained in accordance with the process and isolating the desired isomer.

The invention also provides a process for the preparation of the compounds of the formula II, in free form or in salt form, which comprises, for example, d) reacting a compound of the formula V with water, if appropriate in the presence of an acid catalyst, or e) reacting a compound of the formula VI with a compound of the formula HO–$CH_2$–C($R_4$)(epoxide) (VIII)

which is known or can be prepared in analogy to corresponding known compounds and in which $R_4$ is as defined for formula I, if appropriate in the presence of a base or a dehydrating agent, or with a compound of the formula

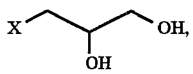

(IX)

which is known or can be prepared in analogy to corresponding known compounds and in which X is halogen, methylsulfonyl or toluenesulfonyl, preferably chlorine or bromine, and/or, if desired, converting a compound of the formula II, in free form or in salt form, which can be obtained in accordance with the process or by a different route into a different compound of the formula II, separating an isomer mixture which can be obtained in accordance with the process and isolating the desired isomer, and/or converting a free compound of the formula II which can be obtained in accordance with the process or by a different route into a salt, or converting a salt of a compound of the formula II which can be obtained in accordance With the process or by a different route into the free compound of the formula II or into a different salt.

The invention also provides a process for the preparation of the compounds of the formula V, which comprises, for example, f) reacting a compound of the formula VI with a compound of the formula

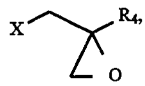

(X)

which is known or can be prepared in analogy to corresponding known compounds and in which $R_4$ is as defined for formula I and X is halogen, methylsulfonyl or toluenesulfonyl, preferably chlorine or bromine, in particular chlorine, if appropriate in the presence of a base catalyst, or g) reacting a compound of the formula

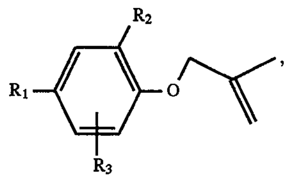

(XI)

which is known or can be prepared in analogy to corresponding known compounds and in which $R_1$, $R_2$ and $R_3$ are as defined for formula I with an oxidant, and/or, if desired, convening a compound of the formula V which can be obtained in accordance with the process or by a different route into a different compound of the formula V and/or separating an isomer mixture which can be obtained in accordance with the process and isolating the desired isomer.

What has been said above for tautomers and/or salts of compounds I, II and V applies analogously to the starting materials mentioned hereinbelow and hereinafter with regard to their tautomers and/or salts.

The reactions described hereinbelow and hereinafter are carried out in a manner known per se, for example in the absence or, if appropriate, in the presence of a suitable solvent or diluent or mixture of these, the process being carried out, if required, with cooling, at room temperature or with heating, for example in a temperature range of approximately −80° C. to the boiling point of the reaction mixture, preferably from approximately −20° C. to approximately +150° C. and, if necessary, in a sealed vessel, under pressure, in an inert gas atmosphere and/or under anhydrous conditions. Particularly advantageous reaction conditions can be seen from the examples.

The starting materials mentioned hereinbelow and hereinafter which are used for the preparation of the compounds I, II and V, in free form or in salt form, are known or can be prepared by methods known per se, for example in accordance with the information given below.

Variant a):

Suitable acid catalysts for facilitating the reaction are, for example, sulfonic acids such as methane- or p-toluenesulfonic acid, camphor-10-sulfonic acid, pyridinio-p-toluenesulfonate, including the acidic ion exchanger resins having sulfo groups, Lewis acids, such as boron trifluoride/diethyl ether or boron trifluoride/dimethyl ether complexes, and also mineral acids such as sulfuric acid or phosphoric acid.

Suitable dehydrating agents for facilitating the elimination of water are, for example, carbodiimides, such as N,N'-dicyclohexylcarbodiimide, or 1-alkyl-2-halopyridinium salts, such as 1-methyl-2-chloropyridinium iodide.

The reactants can be reacted with each other in pure form, i.e. without an addition of a solvent or diluent, for example in the melt. However, in most cases, the addition of an inert solvent or diluent or of a mixture of these is advantageous. Examples of solvents or diluents which may be mentioned are: aromatic, aliphatic and alicyclic hydrocarbons and halohydrocarbons, such as benzene, toluene, xylene, chlorobenzene, bromobenzene, petroleum ether, hexane, cyclohexane, dichloromethane, trichloromethane, dichloroethane or trichloroethene; ethers, such as diethyl ether, tert-butyl methyl ether, tetrahydrofuran or dioxane; amides, such as N,N-dimethylformamide, N,N-dimethylacetamide, N-methylpyrrolidone or hexamethylphosphoric triamide; nitriles, such as acetonitrile; and sulfoxides such as dimethyl sulfoxide.

The reaction is advantageously carried out in a temperature range of approximately 20° C. to approximately +150° C., preferably from approximately +40° C. to approximately 130° C., in many cases at the reflux temperature of the solvent used.

In a preferred embodiment of variant a), a compound II is reacted with a compound III or IV at reflux temperature in an aromatic hydrocarbon, preferably toluene, and in the presence of a sulfonic acid as catalyst, preferably in the presence of p-toluenesulfonic acid, it also being possible for an excess of the compounds III or IV to be employed.

The compounds of the formula III are known or can be prepared in analogy to known compounds.

The compounds IV are known or can be prepared in analogy to known compounds.

Variant b):

A suitable acid catalyst for facilitating the reaction is, for example, acid clay, in particular montmorillonite.

The reactants can be reacted with each other in pure form, i.e. without an addition of a solvent or diluent, for example in the melt. However, in most cases, the addition of an inert solvent or diluent or of a mixture of these is advantageous. Examples of solvents or diluents which may be mentioned are: aromatic, aliphatic and alicyclic hydrocarbons and halohydrocarbons, such as benzene, toluene, xylene, chlorobenzene, bromobenzene, petroleum ether, hexane, cyclohexane, dichloromethane, trichloromethane, dichloroethane or trichloroethene; ethers, such as diethyl ether, tert-butyl methyl ether, tetrahydrofuran or dioxane; amides, such as N,N-dimethylformamide, N,N-dimethylacetamide, N-methylpyrrolidone or hexamethylphosphoric triamide; nitriles, such as acetonitrile; and sulfoxides such as dimethyl sulfoxide.

The reaction is advantageously carried out in a temperature range of approximately 0° C. to approximately +150° C., preferably from approximately +20° C. to approximately +100° C., in many cases at the reflux temperature of the solvent used.

The compounds of the formula III are known or can be prepared in analogy to known compounds.

Variant c):

Suitable leaving groups X in compound VII are, for example, $C_1$–$C_8$alkanesulfonyloxy, halo- $C_1$–$C_8$alkanesulfonyloxy, benzenesulfonyloxy, toluenesulfonyloxy and halogen. $C_1$–$C_8$Alkoxy and halogen are preferred, chlorine and bromine are particularly preferred, and chlorine is very particularly preferred.

Suitable bases for facilitating the reaction are, for example, the hydroxides, hydrides, amides, alkanolates, carbonates, dialkylamides or alkylsilylamides of alkali metals or alkaline earth metals, or alkylamines, alkylenediamines, free or N-alkylated, saturated or unsaturated cycloalkylamines, basic heterocycles, ammonium hydroxides and carbocyclic mines. Examples which may be mentioned are sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, trimethylamine, triethylenediamine, cyclohexylamine, N-cyclohexyl-N,N-dimethylamine, N,N-diethylaniline, pyridine, 4-(N,N-dimethylamino)pyridine, N-methylmorpholine, tetramethylammonium hydroxide, benzyltrimethylammonium hydroxide and 1,5-diazabicyclo[5.4.0]undec-5-ene (DBU). Alkali metal carbonates are particularly suitable.

The reactants can be reacted with each other in pure form, i.e. without an addition of a solvent or diluent, for example in the melt. However, in most cases, the addition of an inert solvent or diluent or of a mixture of these is advantageous. Examples of solvents or diluents which may be mentioned are: aromatic, aliphatic and alicyclic hydrocarbons and halohydrocarbons, such as benzene, toluene, xylene, chlorobenzene, bromobenzene, petroleum ether, hexane, cyclohexane, dichloromethane, trichloromethane, dichloroethane or trichloroethene; ethers, such as diethyl ether, tert-butyl methyl ether, tetrahydrofuran or dioxane; amides, such as N,N-dimethylformamide, N,N-dimethylacetamide, N-methylpyrrolidone or hexamethylphosphoric triamide; nitriles, such as acetonitrile; and sulfoxides such as dimethyl sulfoxide.

The reaction is advantageously carried out in a temperature range of approximately 20° C. to approximately +150° C., preferably from approximately +50° C. to approximately +100° C., in many cases at the reflux temperature of the solvent used.

The compounds of the formula VII are known or can be prepared in analogy to known compounds.

Variant d):

Suitable acid catalysts for facilitating the reaction are, for example, sulfonic acids such as methane- or p-toluenesulfonic acid, camphor-10-sulfonic acid, pyridinio-p-toluenesulfonate, including the acidic ion exchanger resins having sulfo groups, Lewis acids, such as boron trifluoride/diethyl ether or boron trifluoride/dimethyl ether complexes, and, in particular, mineral acids such as sulfuric acid or phosphoric acid.

The reaction can be carried out in water or, preferably, in water/alcohol or water/ether mixtures, in particular in water/tetrahydrofuran mixtures.

The reaction is advantageously carried out in a pH range of the reaction mixture of 0 to 5, preferably 1 to 4, particularly preferably 2 to 3.

The reaction is advantageously carried out in a temperature range of approximately 0° C. to approximately +150° C., preferably from approximately +20° C. to approximately +100° C., in many cases at the reflux temperature of the solvent used.

Variant e):

Suitable bases for facilitating the reaction are, for example, the hydroxides, hydrides, amides, alkanolates, carbonates, dialkylamides or alkylsilylamides of alkali metals or alkaline earth metals, or alkylamines, alkylenediamines, free or N-alkylated, saturated or unsaturated cycloalkylamines, basic heterocycles, ammonium hydroxides and carbocyclic amines. Examples which may be mentioned are sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, trimethylamine, triethylenediamine, cyclohexylamine, N-cyclohexyl-N,N-dimethylamine, N,N-diethylaniline, pyridine, 4-(N,N-dimethylamino)pyridine, N-methylmorpholine, tetramethylammonium hydroxide, benzyltrimethylammonium hydroxide and 1,5-diazabicyclo[5.4.0]undec-5-ene (DBU). Ammonium hydroxides or alkali metal carbonates are particularly suitable, tetramethylammonium hydroxide or potassium carbonate are very particularly suitable.

The reactants can be reacted with each other in pure form, i.e. without an addition of a solvent or diluent, for example in the melt. However, in most cases, the addition of an inert solvent or diluent or of a mixture of these is advantageous. Examples of solvents or diluents which may be mentioned are: aromatic, aliphatic and alicyclic hydrocarbons and halohydrocarbons, such as benzene, toluene, xylene, chlorobenzene, bromobenzene, petroleum ether, hexane, cyclohexane, dichloromethane, trichloromethane, dichloroethane or trichloroethene; ethers, such as diethyl ether, tert-butyl methyl ether, tetrahydrofuran or dioxane; amides, such as N,N-dimethylformamide, N,N-dimethylacetamide, N-methylpyrrolidone or hexamethylphosphoric triamide; nitriles, such as acetonitrile; and sulfoxides such as dimethyl sulfoxide.

The reaction is advantageously carried out in a temperature range of approximately 20° C. to approximately +150° C., preferably from approximately +50° C. to approximately +100° C., in many cases at the reflux temperature of the solvent used.

The compounds of the formula VIII are known or can be prepared in analogy to known compounds.

The compounds of the formula IX are known or can be prepared in analogy to known compounds.

Variant f):

Suitable bases for facilitating the reaction are, for example, the hydroxides, hydrides, amides, alkanolates, carbonates, dialkylamides or alkylsilylamides of alkali metals or alkaline earth metals, or alkylamines, alkylenediamines, free or N-alkylated, saturated or unsaturated cycloalkylamines, basic heterocycles, ammonium hydroxides and carbocyclic amines. Examples which may be mentioned are sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, trimethylamine, triethylenediamine, cyclohexylamine, N-cyclohexyl-N,N-dimethylamine, N,N-diethylaniline, pyridine, 4-(N,N-dimethylamino)pyridine, N-methylmorpholine, tetramethylammonium hydroxide, benzyltrimethylammonium hydroxide and 1,5-diazabicyclo[5.4.0]undec-5-ene (DBU). Alkali metal carbonates are particularly suitable, potassium carbonate is very particularly suitable.

The reactants can be reacted with each other in pure form, i.e. without an addition of a solvent or diluent, for example in the reek. However, in most cases, the addition of an inert solvent or diluent or of a mixture of these is advantageous. Examples of solvents or diluents which may be mentioned are: aromatic, aliphatic and alicyclic hydrocarbons and halohydrocarbons, such as benzene, toluene, xylene, chlorobenzene, bromobenzene, petroleum ether, hexane, cyclohexane, dichloromethane, trichloromethane, dichloroethane or trichloroethene; ethers, such as diethyl ether, tert-butyl methyl ether, tetrahydrofuran or dioxane; amides, such as N,N-dimethylformamide, N,N-dimethylacetamide, N-methylpyrrolidone or hexamethylphosphoric triamide; nitriles, such as acetonitrile; and sulfoxides such as dimethyl sulfoxide.

The reaction is advantageously carried out in a temperature range of approximately 40° C. to approximately +180° C., preferably from approximately +60° C. to approximately +150° C., in many cases at the reflux temperature of the solvent used.

The reactants can be reacted with each other in molar amounts, an excess of compound X being preferred.

The compounds of the formula X are known or can be prepared in analogy to known compounds.

Variant g):

Suitable oxidants are, for example, organic percarboxylic acids, such as peracetic acid, perbenzoic acid or preferably substituted perbenzoic acids, particularly 3-chloroperbenzoic acid.

The reactants can be reacted with each other in pure form, i.e. without an addition of a solvent or diluent, for example in the melt. However, in most cases, the addition of an inert solvent or diluent or of a mixture of these is advantageous. Examples of solvents or diluents which may be mentioned are: aromatic, aliphatic and allcyclic hydrocarbons and halohydrocarbons, such as benzene, toluene, xylene, chlorobenzene, bromobenzene, petroleum ether, hexane, cyclohexane, dichloromethane, trichloromethane, dichloroethane or trichloroethene; ethers, such as diethyl ether, tert-butyl methyl ether, tetrahydrofuran or dioxane; amides, such as N,N-dimethylformamide, N,N-dimethylacetamide, N-methylpyrrolidone or hexamethylphosphoric triamide; nitriles, such as acetonitrile; and sulfoxides such as dimethyl sulfoxide.

The reaction is advantageously carried out in a temperature range of approximately 20° C. to approximately +150° C., preferably from approximately +40° C. to approximately 130° C., in many cases at the reflux temperature of the solvent used.

The compounds I, II and V can exist in the form of one of the isomers which are possible or as a mixture of these, for example as pure isomers, such as antipodes and/or diastereomers, or as isomer mixtures, such as enantiomer mixtures, for example racemates, diastereomer mixtures or racemate mixtures, depending on the number and the absolute and relative configuration of the asymmetric carbon atoms; the invention relates to the pure isomers and also to all isomer mixtures which are possible and is to be understood accordingly in each case hereinabove and hereinbelow even when stereochemical details are not mentioned specifically in each individual case.

Diastereomer mixtures and racemate mixtures of compounds I, II and V which can be obtained in accordance with the process—depending on the choice of starting materials and procedures—or via other routes can be resolved in the known manner on the basis of the physico-chemical differences of the components to give the pure diastereomers or racemates, for example by fractional crystallization, distillation and/or chromatography.

Enantiomer mixtures which can be obtained accordingly, such as racemates, can be separated by known methods to give the optical antipodes, for example by recrystallization from an optically active solvent, by chromatography on chiral adsorbants, for example high-pressure liquid chromatography (HPLC) on acetylcellulose, with the aid of suitable microorganisms, by cleavage using specific, immobilized enzymes, via the formation of inclusion compounds, for example using chiral crown ethers, during which process only one enantiomer is complexed. Pure diastereomers or enantiomers can be obtained according to the invention not only by resolving appropriate isomer mixtures, but also by generally known methods of diastereoselective or enantioselective synthesis, for example by carrying out the process according to the invention using educts of a suitable stereochemistry.

If the individual components differ with regard to their biological activity, it is advantageous to isolate, or synthesize, the isomer, for example enantiomer, or isomer mixture, for example enantiomer mixture, which has the higher biological activity in each case.

The compounds I, II and V can also be obtained in the form of their hydrates and/or include other solvents, for example solvents which, if desired, have been used for the crystallization of compounds which are present in solid form.

The invention relates to all those embodiments of the process in which, starting from a compound which can be obtained at any stage of the process as starting material or intermediate, all or some of the missing steps are carried out, or in which a starting material is used in the form of a derivative or salt and/or its racemates or antipodes or, in particular, is formed under the reaction conditions.

In the process of the present invention, starting substances and intermediates which are preferably used are those which lead to the compounds I which have been described at the outset as being particularly valuable.

In particular, the invention relates to the preparation processes described in Examples H1 to H5.

The invention also provides novel starting substances and intermediates which are used according to the invention for the preparation of the compounds I, to their use, and to processes for their preparation.

The present invention also provides the compounds II and V, which are of specific importance in this context, and to their preparation and their use as intermediates.

The compounds I according to the invention are valuable active ingredients for preventive and/or curative use in the field of pest control, even when used at low rates of concentration, which have a very advantageous biocidal spectrum while being well tolerated by warm-blooded species, fish and plants. The active ingredients according to the invention are effective against all or individual development stages of normally-sensitive, but also resistant, animal pests, such as insects or representatives of the order Acarina. The insecticidal or acaricidal activity of the active ingredients according to the invention may become apparent directly, i.e. from a destruction of the pests, either immediately or only after some time has elapsed, for example during molting, or indirectly, for example from a reduced oviposition and/or hatching rate, the good activity corresponding to a mortality rate of not less than 50 to 60%.

The abovementioned animal pests include, for example: from the order Lepidoptera, for example,

*Acleris spp., Adoxophyes spp., Aegeria spp., Agrotis spp., Alabama argillaceae, Amylois spp., Anticarsia gemmatalis, Archips spp., Argyrotaenia spp., Autographa spp., Busseola fusca, Cadra cautella, Carposina nipponensis, Chilo spp., Choristoneura spp., Clysia ambiguella, Cnaphalocrocis spp., Cnephasia spp., Cochylis spp., Coleophora spp., Cro-* cidolomia binotalis, Cryptophlebia leucotreta, Cydia spp., Diatraea spp., Diparopsis castanea, Earias spp., Ephestia spp., Eucosma spp., Eupoecilia ambiguella, Euproctis spp., Euxoa spp., Grapholita spp., Hedya nubiferana, Hellothis spp., Hellula undalis, Hyphantria cunea, Keiferia lycopersicella, Leucoptera scitella, Lithocollethis spp., Lobesia botrana, Lymantria spp., Lyonefta spp., Malacosoma spp., Mamestra brassicae, Manduca sexta, Operophtera spp., Ostrinia nubilalis, Pammene spp., Pandemis spp., Panolis flammea, Pectinophora gossypiella, Phthorimaea operculella, Pieris rapae, Pieris spp., Plutella xylostella, Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;* from the order Coleoptera, for example, *Agriotes spp., Anthonomus spp., Atomaria linearis, Chaetocnema tibialis, Cosmopolites spp., Curculio spp., Dermestes spp., Diabrotica spp., Epilachna spp., Eremnus spp., Leptinotarsa decemlineata, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophihs spp., Sitotroga spp., Tenebrio spp., Tribolium spp.* and *Trogoderma spp.;* from the order Orthoptera, for example,

*Blatta spp., Blattella spp., Gryllotalpa spp., Leucophaea maderae, Locusta spp., Periplaneta spp.* and *Schistocerca spp.;* from the order Isoptera, for example

*Reticulitermes spp.;* from the order Psocoptera, for example

*Liposcelis spp.;* from the order Anoplura, for example,

*Haematopinus spp., Linognathus spp., Pediculus spp., Pemphigus spp.* and *Phylloxera spp.;* from the order Mallophaga, for example,

*Damalinea spp.* and *Trichodectes spp.;* from the order Thysanoptera, for example,

*Franklinlella spp., Hercinothrips spp., Taeniothrips spp., Thrips palmi, Thrips tabaci* and *Scirtothrips aurantii;* from the order Heteroptera, for example,

*Cimex spp., Distantleila theobroma, Dysdercus spp., Euchistus spp. Eurygaster spp. Leptocorisa spp., Nezara spp., Piesma spp., Rhodnius spp., Sahlbergella singularis, Scotinophara spp.* and *Triatoma spp.;* from the order Homoptera, for example,

*Aleurothrixus floccosus, Aleyrodes brassicae, Aonidiella spp., Aphididac, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae* and *Unaspis citri;* from the order Hymenoptera, for example,

*Acromyrmex, Atta spp., Cephus spp., Diprion spp., Diprionidae, Gilpinia polytoma, Hoplocampa spp., Lasius spp., Monomorium pharaonis, Neodiprion spp., Solenopsis spp.* and *Vespa spp.;* from the order Diptera, for example,

*Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp.* and *Tipula spp.;* from the order Siphonaptera, for example,

*Ceratophyllus spp.* and *Xenopsylla cheopis;* from the order Thysanura, for example

*Lepisma saccharina* and from the order Acarina, for example,

*Acarus siro, Aceria sheldoni, Aculus schlechtendali, Amblyomma spp., Argas spp., Boophilus spp., Brevipalpus spp., Bryobia praetiosa, Calipitrimerus spp., Chorioptes spp., Dermanyssus gallinae, Eotetranychus carpini, Eriophyes spp., Hyalomma spp., Ixodes spp., Olygonychus pratensis, Ornithodoros spp., Panonychus spp., Phyllocoptruta oleivora, Polyphagotarsonemus latus, Psoroptes spp., Rhipicephalus spp., Rhizoglyphus spp., Sarcoptes spp., Tarsonemus spp.* and *Tetranychus spp.*.

The active ingredients according to the invention are particularly suitable for controlling, i.e. containing or destroying, pests of the abovementioned type which are found on plants, especially on crop plants and ornamentals in agriculture, horticulture and silviculture, or on parts of such plants, such as fruits, flowers, foliage, stalks, tubers or roots, and even parts of plants which are formed at a later point in time are protected against these pests in some cases.

Target crops which are possible are, in particular, cereals, such as wheat, barley, rye, oats, rice, maize or sorghum; beet, such as sugar or fodder beet; fruit, for example pome fruit, stone fruit and soft fruit, such as apples, pears, plums, peaches, almonds, cherries or berries, for example strawberries, raspberries or blackberries; pulses, such as beans, lentils, peas or soya beans; oil crops, such as oilseed rape, mustard, poppy, olives, sunflowers, coconut, castor, cocoa or groundnuts; cucurbits, such as pumpkins, cucumbers or melons; fibre plants, such as cotton, flax, hemp or jute; citrus fruits, such as oranges, lemons, grapefruit or tangerines; vegetables, such as spinach, lettuce, asparagus, cabbages, carrots, onions, tomatoes, potatoes or bell peppers; the laurel family, such as avocado, Cinnamonium or camphor; and also tobacco, nuts, coffee, eggplants, sugar cane, tea, pepper, grapevines, hops, the banana family, latex plants and ornamentals.

Other fields of application for the active ingredients according to the invention are the protection of stored products and stores, and of material, and also, in the hygiene sector, in particular the protection of domestic animals and productive livestock against pests of the abovementioned type.

The invention therefore also relates to pesticides such as emulsifiable concentrates, suspension concentrates, directly sprayable or dilutable solutions, spreadable pastes, dilute emulsions, wettable powders, soluble powders, dispersible powders, wettable powders, dusts, granules or encapsulations in polymeric substances, all of which comprise—not less than—one of the active ingredients according to the invention and which are to be selected to suit the intended aims and the prevailing circumstances.

In these compositions, the active ingredient is employed in pure form, for example a solid active ingredient in a specific particle size, or, preferably, together with not less than one of the auxiliaries conventionally used in the art of formulation, such as extenders, for example solvents or solid carriers, or surface-active compounds (surfactants).

Examples of suitable solvents are the following: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and their ethers and esters, such as propylene glycol, dipropylene glycol ether, ethylene glycol, ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unepoxidized or epoxidized rapeseed oil, castor oil, coconut oil or soya oil, and also silicone oils.

As a rule, solid carriers which are used for example for dusts and dispersible powders are ground natural minerals such as calcite, talc, kaolin, montmorillonite or attapulgite. To improve the physical properties, it is also possible to add highly-disperse silicas or highly-disperse absorptive polymers. Possible particulate, adsorptive carriers for granules are porous types, such as pumice, brick grit, sepiolite or bentonite, or non-sorptive carrier materials, for example calcite or sand. Moreover, a large number of granulated materials of inorganic or organic nature can be used such as, in particular, dolomite or comminuted plant residues.

Suitable surface-active compounds are non-ionic, cationic and/or anionic surfactants or surfactant mixtures which have good emulsifying, dispersing and wetting properties, depending on the nature of active ingredient to be formulated. The surfactants listed below are only to be regarded as examples; a large number of other surfactants which are conventionally used in the art of formulation and suitable in accordance with the invention are described in the specialist literature.

Suitable non-ionic surfactants are mainly polyglycol ether derivatives of aliphatic or cycloaliphatic alcohols, saturated or unsaturated fatty acids and alkylphenols, which can have 3 to 30 glycol ether groups and 8 to 20 carbon atoms in the (aliphatic) hydrocarbon radical and 6 to 18 carbon atoms in the alkyl radical of the alkylphenols. Other suitable non-ionic surfactants are water-soluble polyethylene oxide adducts with polypropylene glycol, ethylene diaminopolypropylene glycol and alkyl polypropylene glycol which have 1 to 10 carbon atoms in the alkyl chain and comprise 20 to 250 ethylene glycol ether groups and 10 to 100 propylene glycol ether groups. The abovementioned compounds customarily have 1 to 5 ethylene glycol units per propylene glycol unit. Examples which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Other substances which are suitable are fatty acid esters of polyoxyethylene sorbitan, such as polyoxyethylene sorbitan trioleate.

The cationic surfactants are mainly quaternary ammonium salts which have, as substituents, at least one alkyl radical having 8 to 22 carbon atoms and as further substituents lower, halogenated or unhalogenated alkyl, benzyl or lower hydroxyalkyl radicals. The salts are preferably in the form of halides, methylsulfates or ethylsulfates. Examples are stearyltrimethylammonium chloride and benzyldi(2-chloroethyl)ethylammonium bromide.

Suitable anionic surfactants can be either water-soluble soaps or water-soluble synthetic surface-active compounds. Soaps which are suitable are the alkali metal salts, alkaline earth metal salts and substituted or unsubstituted ammonium salts of higher fatty acids ($C_{10}$–$C_{22}$), such as the sodium or potassium salts of oleic or stearic acid, or of natural fatty acid mixtures which can be obtained from, for example, coconut oil or tall oil; mention must also be made of the fatty acid methyltaurides. However, synthetic surfactants are used more frequently, in particular fatty sulfonates, fatty sulfates, sulfonated benzimidazole derivatives or alkylarylsulfonates. The fatty sulfonates and fatty sulfates are, as a rule, in the form of alkali metal salts, alkaline earth metal salts or substituted or unsubstituted ammonium salts and have, as a rule, an alkyl radical having 8 to 22 carbon atoms, alkyl also including the alkyl moiety of acyl radicals; examples which may be mentioned are the sodium or calcium salt of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives have preferably 2 sulfonyl groups and a fatty acid radical having approximately 8 to 22 carbon atoms. Examples of alkylarylsulfonates are the sodium, calcium or triethanolammonium salts of dodecylbenzenesulfonic acid, of dibutylnaphthalenesulfonic acid or of a naphthalenesulfonic acid/formaldehyde condensation product. Suitable phosphates, for example salts of the phosphoric ester of a p-nonylphenol/(4–14)ethylene oxide adduct, or phospholipids, are also suitable.

As a rule, the compositions comprise 0.1 to 99%, in particular 0.1 to 95%, of active ingredient and 1 to 99.9%, in particular 5 to 99.9%, of not less than one solid or liquid auxiliary, the surfactant content of the compositions amounting to, as a rule, 0 to 25%, in particular 0.1 to 20% (% means in each case per cent by weight). While concentrated compositions are generally more preferred as commercially available goods, the end consumer uses, as a rule, dilute compositions having considerably lower concentrations of active ingredient. Preferred compositions are, in particular, composed as follows (% =percent by weight):

| | |
|---|---|
| Emulsifiable concentrates: | |
| Active ingredient: | 1 to 90%, preferably 5 to 20% |
| Surfactant: | 1 to 30%, preferably 10 to 20% |
| Solvent: | 5 to 98%, preferably 70 to 85% |
| Dusts: | |
| Active ingedient: | 0.1 to 10%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surfactant: | 1 to 40%, preferably 2 to 30% |
| Wettable powders: | |
| Active ingredient: | 0.5 to 90%, preferably 1 to 80% |
| Surfactant: | 0.5 to 20%, preferably 1 to 15% |
| Solid carrier: | 5 to 99%, preferably 15 to 98% |
| Granules: | |
| Active ingredient: | 0.5 to 30%, preferably 3 to 15% |
| Solid carrier: | 99.5 to 70%, preferably 97 to 95% |

The action of the compositions according to the invention can be broadened considerably and adapted to suit prevailing circumstances by adding other insecticidal or acaricidal active ingredients. Possible as additions of insecticidal or acaricidal active ingredients are, for example, representatives of the following active ingredient classes: organophosphorus compounds, nitrophenols and derivatives, formamidines, acylureas, carbamates, pyrethroids, nitroenamines and derivatives, pyrroles, thioureas and derivatives, chlorinated hydrocarbons and *Bacillus thuringiensis* preparations. The compositions according to the invention can also comprise other solid or liquid auxiliaries, such as stabilizers, for example epoxidized or unepoxidized vegetable oils (for example epoxidized coconut oil, rapeseed oil or soya oil), antifoams, for example silicone oil, preservatives, viscosity regulators, binders and/or tackifiers, and also fertilizers or other active ingredients for achieving specific effects, for example bactericides, fungicides, nematicides, molluscicides or selective herbicides.

The compositions according to the invention are prepared in a known manner, for example, in the absence of auxiliaries, by grinding, screening and/or compressing a solid active ingredient or active ingredient mixture, for example to a certain particle size, and, in the presence of at least one auxiliary, for example by intimately mixing and/or grinding the active ingredient or active ingredient mixture with the auxiliary or the auxiliaries. These processes for the preparation of the compositions according to the invention and the use of the compounds I for the preparation of these compositions are also a subject which the invention relates to.

The invention furthermore relates to the methods of application for the compositions, i.e. the methods for controlling pests of the abovementioned type such as spraying, atomizing, dusting, brushing on, seed dressing, scattering or pouring, which are to be selected as a function of the intended aims and the prevailing circumstances, and to the use of the compositions for controlling pests of the abovementioned type. Typical rates of concentration are between 0.1 and 1000 ppm, preferably between 0.1 and 500 ppm, of active ingredient. The rates of application per hectare are, as a rule, 1 to 2000 g of active ingredient per hectare, in particular 10 to 1000 g/ha, preferably 20 to 600 g/ha.

A preferred method of application in the field of crop protection is application to the foliage of the plants (foliar application); frequency and rate of application will be matched to the risk of infestation with the pest in question. Alternatively, the active ingredient can reach the plants via the root system (systemic action), by drenching the locus of the plants with a liquid composition or introducing the active ingredient in solid form to the locus of the plants, for example the soil, for example in the form of granules (soil application). In the case of paddy rice, such granules can be metered into the flooded paddy field.

The compositions according to the invention are also suitable for protecting plant propagation material, for example seed, such as fruits, tubers or grains, or nursery plants, against animal pests. The propagation material can be treated with the composition before planting, for example seed may be dressed before sowing. It is also possible to apply the active ingredients according to the invention to seeds (coating), either by soaking the kernels in a liquid composition or by coating them with a solid composition. Alternatively, when the propagation material is planted, the composition may be applied to the locus of planting, for example to the seed furrow in the case of sowing. These treatment methods for plant propagation material and the plant propagation material which has been treated in this manner are further subjects which the invention relates to.

The examples which follow are intended to illustrate the invention. They do not limit the invention. Temperatures are given in degree centigrade. "$n_D^T$" indicates the refractive index at a temperature of T°C. "m.p." indicates the melting point. "%" indicates percent by weight, unless otherwise defined.

PREPARATION EXAMPLES

Example H1

2-Chloro-4-(1-methylpropoxy)phenol

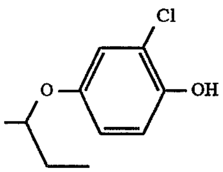

76.8 g of sulfuryl chloride are added dropwise with stirring at 0° to 5° C. in the course of approximately 30 minutes to a solution of 91.3 g of 4-(1-methylpropoxy)phenol in 900 ml of dichloromethane. Stirring is subsequently continued for 14 hours at room temperature. Thereupon, the reaction mixture is evaporated completely in vacuo, and the residue is chromatographed on silica gel (eluent: diethyl ether/n-hexane 1:9), resulting in the pure product of a refractive index $n_D^{20}$ of 1.5321.

The following compound can be prepared analogously:

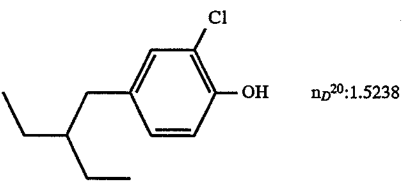

Example H2

2,6-Dibromo-4-(1-methylpropoxy)phenol

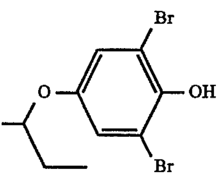

48 g of bromine are added dropwise with stirring at 0° to 5° C. in the course of 2 hours to a solution of 24.9 g of 4-(1-methylpropoxy)phenol in 120 ml of dichloromethane. The mixture is subsequently heated to 20°–22° C. and stirred at this temperature for a further 10 hours. Thereupon, the reaction mixture is evaporated in vacuo, and the residue is purified by chromatography on silica gel (eluent: diethyl ether/n-hexane 1:5), resulting in the pure product of a refractive index $n_D^{20}$ of 1.5780.

The following compound can be prepared analogously:

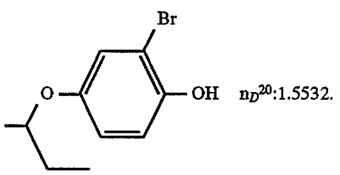

Example H3

3-[2-Chloro-4-(1-methylpropoxy)phenoxy]1,2-propanediol

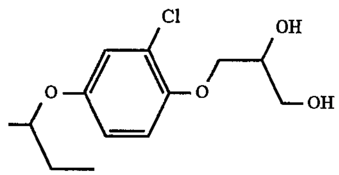

0.3 g of tetramethylammonium chloride is added to a solution of 40.1 g of 2-chloro-4-(1-methylpropoxy)phenol in 300 ml of xylene, the mixture is heated to 60° C., and 16.3 g of glycidol are added dropwise with stirring in the course of approximately 30 minutes. Thereupon, stirring of the reaction mixture is continued for 10 hours at 90° C. To isolate the product, the solvent is distilled off in vacuo using a rotary evaporator and the residue is chromatographed on silica gel (eluent: diethyl ether/methylene chloride 1:2), resulting in the pure product of a refractive index $n_D^{20}$ of 1.5330.

The following compounds can be prepared analogously:

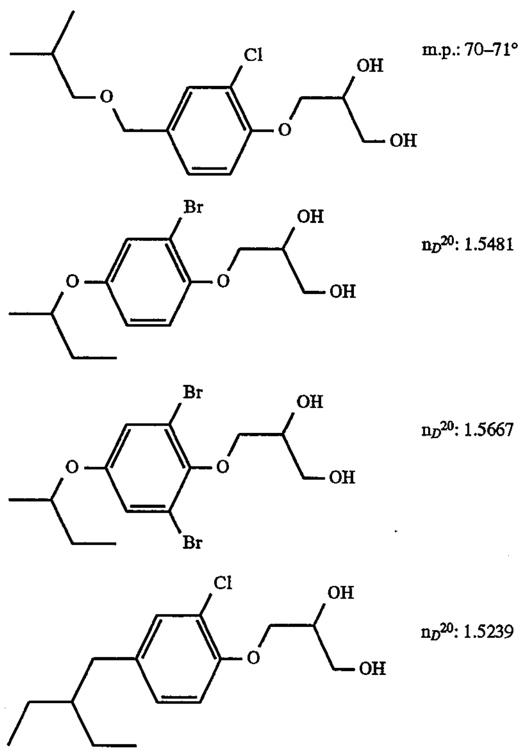

All examples mentioned in Tables 5 to 8 can also be prepared analogously.

Example H4

2-Ethyl-4-[2-chloro-4-(1-methylpropoxy)phenoxymethyl]-1,3-dioxolane

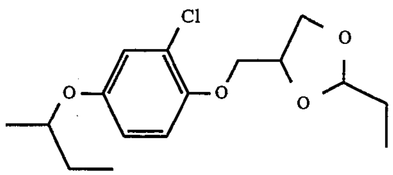

2.4 g of freshly distilled propionaldehyde are added with stirring to a solution of 8.2 g of 3-[2-chloro-4-(1-methylpropoxy)phenoxy]-1,2-propanediol and 30 mg of 4-toluenesulfonic acid in 80 ml of toluene, and the reaction mixture is stirred for 2 hours at reflux temperature. Thereupon, the reaction mixture is washed repeatedly using 10% sodium carbonate solution and subsequently water, and the toluene solution is dried over sodium sulfate, the solvent is distilled off completely in vacuo, and the residue is chromatographed on silica gel (eluent: diethyl ether/n-hexane 1:9), resulting in the isolation of two diastereomers A and B.

In each case two diastereomers A and B of the following compounds can be prepared analogously:

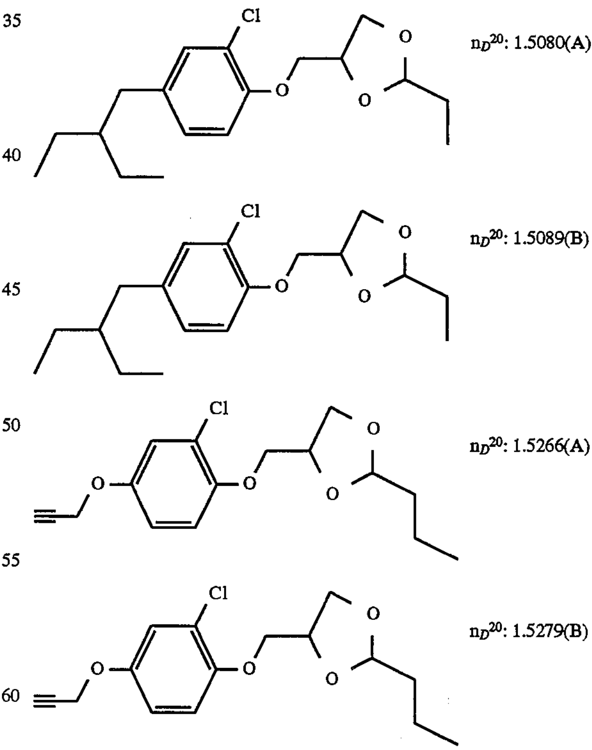

All examples mentioned in Tables 1 to 4 can also be prepared analogously.

Example H5

1 -Benzyloxy-4-(2-methylpropoxymethyl)benzene

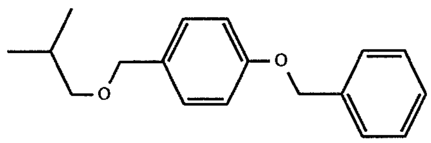

A solution of 74.9 g of 4-benzyloxybeuzyl alcohol, 19 g of tetrabutylammonium hydrogen sulfate and 224 g of 50% sodium hydroxide solution in 300 ml of toluene is stirred for 15 minutes at 40°. At this temperature, 192 g of isobutyl bromide are subsequently added dropwise in the course of 2 hours, and the mixture is stirred at the same temperature for a further 20 hours. Then, the reaction mixture is poured into ice-water, the organic phase is separated off, and the aqueous phase is extracted repeatedly using toluene. The combined organic phases are washed with water until neutral, dried using sodium sulfate and evaporated. After purification of the residue on silica gel using diethyl ether/n-hexane (1:19), the pure title compound of a refractive index $n_D^{20}$ of 1.5399 is obtained.

Example H6

4-(2-Methylpropoxymethyl)phenol

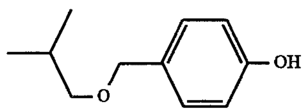

1 g of palladium/charcoal (5% of Pd) is added to a solution of 108 g of 1-benzyloxy-4-(2-methylpropoxymethyl)benzene and 216 ml of triethylamine in 870 ml of tetrahydrofuran, and the mixture is subjected to hydrogenolysis in a hydrogenation apparatus under a super-atmospheric pressure of 100 mbar and at room temperature, 8.93 liters of hydrogen being taken up in the course of 4 hours with hydrogen. The suspension is subsequently filtered through diatomaceous earth, the solvent is then distilled off, and the residue is chromatographed on silica gel using diethyl ether/n-hexane (1:3), resulting in the isolation of 69.3 g of the title compound of a refractive index $n_D^{20}$ of 1.5139.

Example H7

2-Chloro-4-(2-methylpropoxymethyl)phenol

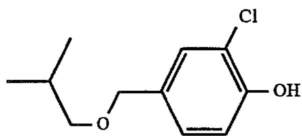

35.8 g of t-butyl hypochlorite are added dropwise with stirring at 0° in the course of 1 hour to a solution of 59.4 g of 4-(2-methylpropoxymethyl)phenol in 500 ml of carbon tetrachloride, the temperature is subsequently allowed to climb to 20°, and the mixture is stirred for a further 30 minutes. The solvent is removed by distillation, the residue is then taken up in ethyl acetate, and the solution is washed twice using aqueous 5% sodium hydrogen carbonate solution and twice using water. The solution is dried using sodium sulfate and evaporated, and the residue is then chromatographed on silica gel using diethyl ether/n-hexane (1:19), resulting in the pure title compound of a refractive index $n_D^{20}$ of 1.5251.

Example H8

2-Ethyl-4-[2-chloro-4-(2-methylpropoxymethyl) phenoxymethyl]-1,3-dioxolane (diastereoisomer mixture)

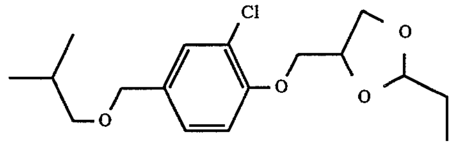

The title compound is obtained from 3-[2-chloro-4-(2-methylpropoxymethyl)phenoxy-1,2-propanediol and propionaldehyde analogously to Example H4 as a diastereoisomer mixture which can be resolved by chromatography on silica gel using diethyl ether/n-hexane (1:19) to give the diastereomers A, of a refractive index $n_D^{20}$ of 1.5035, and B, of a refractive index $n_D^{20}$ of 1.5044.

Example H9

4-(2-Ethylpropanoyl)anisole

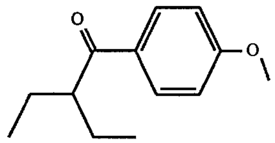

32 g of aluminium trichloride are added with stirring to a solution of 21.6 g of anisole in 180 ml of dichloromethane, the mixture is cooled to −10°, and 28.2 g of 2-ethylbutyryl chloride am added dropwise with stirring in the course of 30 minutes. After the reaction mixture has been stirred for a further hour at −10°, the temperature is allowed to climb to 0°, and the reaction mixture is poured into a mixture of 30 ml of 37% hydrochloric acid and 600 ml of ice-water. The organic phase is separated off, and the aqueous phase is extracted three times using dichloromethane. The combined organic phases are subsequently washed using 1N sodium hydroxide solution and then repeatedly using water, dried over sodium sulfate and then evaporated. In this manner, 38 g of pure title compound of a refractive index $n_D^{20}$ of 1.5226 are obtained by chromatography on silica gel using diethyl ether/n-hexane (1:9).

Example H10

4-(2-Ethylbutyl)phenol

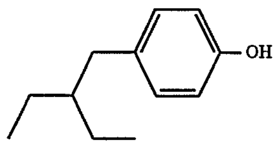

A mixture of 16.5 g of 4-(2-ethylpropanoyl)anisole, 16 g of hydrazine hydrate, 160 ml of triethylene glycol and 18 g of finely powdered potassium hydroxide is heated slowly to 190°–200° under a protective gas atmosphere with stirring, and the water of reaction which evaporates and a small amount of hydrazine hydrate are condensed using a descending condenser. After the reaction mixture has been stirred for 6 hours at 200°, it is cooled to room temperature, water is added, and the mixture is extracted repeatedly using t-butyl methyl ether. The combined organic phases are subsequently washed repeatedly using 1N hydrochloric acid and then water, dried over sodium sulfate and evaporated. Purification by chromatography on silica gel with diethyl ether/n-hexane (1:9) gives the pure title compound of a refractive index $n_D^{20}$ of 1.5163.

Example H11

The other compounds mentioned in Tables 1 to 4 can also be prepared analogously to the procedure described in Examples H4 and H8. The intermediates mentioned in Tables 5 to 8 can be prepared analogously to the procedure described in Example H3 from known starting materials or starting materials which can be prepared analogously to known compounds. In the column "physical data" of these tables, "$n_D^{20}$" symbolizes the refractive index of the compound in question, the melting points ("m.p.") are given in °C. Where indicated, A and B symbolize the diastereomers.

TABLE 1

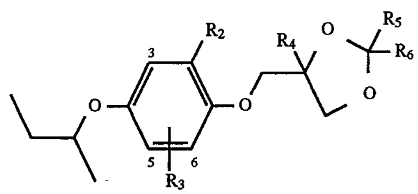

| Comp. No. | $R_2$ | $R_3$ | $R_4$ | $R_5$ | $R_6$ | Physical data |
|---|---|---|---|---|---|---|
| 1.1 | Cl | H | H | H | $C_2H_5$ | |
| 1.1A | Cl | H | H | H | $C_2H_5$ | $n_D^{20}$:1.5092 |
| 1.1B | Cl | H | H | H | $C_2H_5$ | $n_D^{20}$:1.5103 |
| 1.2 | Cl | H | H | H | $C_3H_7$ | |
| 1.2A | Cl | H | H | H | $C_3H_7$ | $n_D^{20}$:1.5069 |
| 1.2B | Cl | H | H | H | $C_3H_7$ | $n_D^{20}$:1.5076 |
| 1.3 | Br | H | H | H | $C_2H_5$ | |
| 1.3A | Br | H | H | H | $C_2H_5$ | $n_D^{20}$:1.5218 |
| 1.3B | Br | H | H | H | $C_2H_5$ | $n_D^{20}$:1.5228 |
| 1.4 | Br | H | H | H | $C_3H_7$ | |
| 1.4A | Br | H | H | H | $C_3H_7$ | $n_D^{20}$:1.5169 |
| 1.4B | Br | H | H | H | $C_3H_7$ | $n_D^{20}$:1.5178 |
| 1.5 | Br | 6-Br | H | H | $C_2H_5$ | |
| 1.5A | Br | 6-Br | H | H | $C_2H_5$ | $n_D^{20}$:1.5420 |
| 1.5B | Br | 6-Br | H | H | $C_2H_5$ | $n_D^{20}$:1.5428 |
| 1.6 | Br | 6-Br | H | H | $C_3H_7$ | |
| 1.6A | Br | 6-Br | H | H | $C_3H_7$ | $n_D^{20}$:1.5374 |
| 1.6B | Br | 6-Br | H | H | $C_3H_7$ | $n_D^{20}$:1.5380 |
| 1.7 | Cl | H | H | i-$C_3H_7$ | H | |
| 1.7A | Cl | H | H | i-$C_3H_7$ | H | $n_D^{20}$:1.5069 |
| 1.7B | Cl | H | H | i-$C_3H_7$ | H | $n_D^{20}$:1.5077 |
| 1.8 | Cl | H | H | i-$C_4H_9$ | H | |
| 1.8A | Cl | H | H | i-$C_4H_9$ | H | $n_D^{20}$:1.5031 |
| 1.8B | Cl | H | H | i-$C_4H_9$ | H | $n_D^{20}$:1.5042 |
| 1.9 | Cl | H | H | sec-$C_4H_9$ | H | |
| 1.10 | Cl | H | H | cyclo-$C_3H_5$ | H | |
| 1.10A | Cl | H | H | cyclo-$C_3H_5$ | H | $n_D^{20}$:1.5209 |
| 1.10B | Cl | H | H | cyclo-$C_3H_5$ | H | $n_D^{20}$:1.5217 |
| 1.11 | Cl | H | H | cyclo-$C_3H_5$ | $CH_3$ | |
| 1.12 | Cl | H | H | H | $OCH_3$ | |
| 1.13 | Cl | H | H | H | $OC_2H_5$ | |
| 1.14 | Cl | H | H | $CH{=}CH_2$ | H | |
| 1.15 | Cl | H | H | $CH{=}CHCl$ | H | |
| 1.16 | Cl | H | H | $CH{=}CHCH_3$ | H | |
| 1.17 | Cl | H | H | $CH{=}C(CH_3)_2$ | H | |
| 1.18 | Cl | H | H | $CH_2CH_2F$ | H | |
| 1.19 | Cl | H | H | $CH_2CH_2Cl$ | H | |
| 1.20 | Cl | H | H | $C{\equiv}CH$ | H | |
| 1.21 | Cl | H | H | $C{\equiv}CI$ | H | |
| 1.22 | Cl | H | H | $C{\equiv}CCH_3$ | H | |
| 1.23 | Cl | H | H | $CH_2C_6H_5$ | H | |
| 1.24 | Cl | H | H | $CH_2CN$ | H | |
| 1.25 | Cl | H | H | $CH_3$ | H | |
| 1.26 | Cl | H | H | $C_8H_{17}$ | H | |
| 1.27 | Cl | H | H | $CH_3$ | i-$C_3H_7$ | |
| 1.28 | Cl | H | H | $CH_3$ | $CH_3$ | |

TABLE 1-continued

| Comp. No. | $R_2$ | $R_3$ | $R_4$ | $R_5$ | $R_6$ | Physical data |
|---|---|---|---|---|---|---|
| 1.29 | Cl | H | H | $CH_3$ | $C_2H_5$ | |
| 1.30 | Cl | H | H | $CH_3$ | $CH{=}H_2$ | |
| 1.31 | Cl | H | H | $CH_3$ | $C{\equiv}CH$ | |
| 1.32 | Cl | H | H | $C_2H_5$ | $C_2H_5$ | |
| 1.33 | Cl | H | H | H | $C_6H_4Cl(4)$ | |
| 1.34 | Cl | H | H | H | $C_6H_3Cl_2(2,4)$ | |
| 1.35 | Cl | H | H | H | 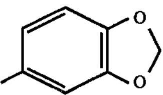 | |
| 1.36 | Cl | H | H | H | $C_6H_4C_2H_5(4)$ | |
| 1.37 | Cl | H | H | H | $C_6H_4OCH_3(4)$ | |
| 1.38 | Cl | H | H | H | $C_6H_4CF_3(4)$ | |
| 1.39 | Cl | H | H | H | $C_6H_4F(4)$ | |
| 1.40 | Cl | H | H | $CH_2-CH_2-CH_2$ | | $n_D^{20}$:1.5198 |
| 1.41 | Cl | H | H | $CH_2-CH_2-CH_2-CH_2$ | | |
| 1.42 | Cl | H | H | $CH_2-CH_2-CH_2-CH_2-CH_2$ | | |
| 1.43 | Cl | H | H | H | cyclopentyl | |
| 1.44 | Cl | H | H | H | 4-pyridyl | |
| 1.45 | Cl | H | H | H | 3-pyridyl | |
| 1.46 | Cl | H | H | H | 2-pyridyl | |
| 1.47 | Cl | H | H | H | 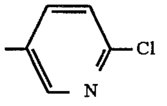 | |
| 1.48 | Cl | H | H | H | 2-furyl | |
| 1.49 | Cl | H | H | H | 3-furyl | |
| 1.50 | Cl | H | $CH_3$ | $C_2H_5$ | H | |
| 1.51 | Cl | H | $CH_3$ | n-$C_3H_7$ | H | |
| 1.52 | Cl | H | $CH_3$ | iso-$C_3H_7$ | H | |
| 1.53 | Cl | H | $CH_3$ | $CH{=}CH_2$ | H | |
| 1.54 | Cl | H | $CH_3$ | cyclo-$C_3H_5$ | H | |
| 1.55 | F | H | H | $CH_3$ | H | |
| 1.56 | F | H | H | $C_2H_5$ | H | |
| 1.57 | F | H | H | n-$C_3H_7$ | H | |
| 1.58 | F | H | H | iso-$C_3H_7$ | H | |
| 1.59 | F | H | H | cyclo-$C_3H_5$ | H | |
| 1.60 | F | H | H | iso-$C_4H_9$ | H | |
| 1.61 | F | H | H | $CH{=}CH_2$ | H | |
| 1.62 | F | H | H | cyclohexyl | H | |
| 1.63 | F | H | H | $CH_2-CH_2-CH_2$ | | |
| 1.64 | F | H | H | $CH_2-CH_2-CH_2-CH_2$ | | |
| 1.65 | F | H | H | $CH_2-CH_2-CH_2-CH_2-CH_2$ | | |
| 1.66 | F | H | H | H | $C_6H_3Cl_2(2,4)$ | |
| 1.67 | F | H | H | H | $C_6H_3Cl_2(3,4)$ | |
| 1.68 | F | H | H | H | $OC_2H_5$ | |
| 1.69 | Br | H | H | $CH_3$ | H | |
| 1.70 | Br | H | H | $C_2H_5$ | H | |
| 1.71 | Br | H | H | n-$C_3H_7$ | H | |
| 1.72 | Br | H | H | iso-$C_3H_7$ | H | |
| 1.73 | Br | H | H | cyclo-$C_3H_5$ | H | |
| 1.74 | Br | H | H | $CH{=}CH_2$ | H | |
| 1.75 | Br | H | H | $CH{=}CHCH_2$ | H | |
| 1.76 | Br | H | H | iso-$C_4H_9$ | H | |
| 1.77 | Br | H | H | $CH_2C_6H_5Cl(4)$ | H | |
| 1.78 | Br | H | H | $CH_2C_6H_5OCH_3(4)$ | H | |
| 1.79 | Br | H | H | $CH_2C_6H_5CH_3(4)$ | H | |
| 1.80 | Br | H | H | $C_2H_4OCH_3$ | H | |
| 1.81 | Br | H | H | $CH{=}CHCl$ | H | |
| 1.82 | Br | H | H | H | $OCH_3$ | |
| 1.83 | Br | H | H | H | $OC_2H_5$ | |

TABLE 1-continued

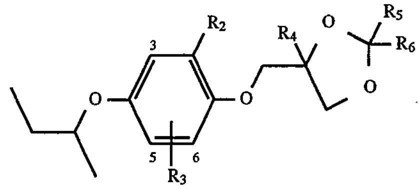

| Comp. No. | $R_2$ | $R_3$ | $R_4$ | $R_5$ | $R_6$ | Physical data |
|---|---|---|---|---|---|---|
| 1.84 | Br | H | H | $CH_3$ | $CH_3$ | |
| 1.85 | Br | H | H | $CH_3$ | $C_2H_5$ | |
| 1.86 | Br | H | H | $CH_3$ | $CH{=}H_2$ | |
| 1.87 | Br | H | H | $C_2H_5$ | $C_2H_5$ | |
| 1.88 | Br | H | H | H | $C_6H_4Cl(4)$ | |
| 1.89 | Br | H | H | H | $C_6H_3Cl_2(3,4)$ | |
| 1.90 | Br | H | H | $CH_2-CH_2-CH_2$ | | |
| 1.91 | Br | H | H | $CH_2-CH_2-CH_2-CH_2$ | | |
| 1.92 | Br | H | $CH_3$ | $C_2H_5$ | H | |
| 1.93 | Br | H | $CH_3$ | n-$C_3H_7$ | H | |
| 1.94 | Br | 6-Br | H | $CH_3$ | H | |
| 1.95 | Br | 6-Br | H | $C_2H_5$ | H | |
| 1.96 | Br | 6-Br | H | n-$C_3H_7$ | H | |
| 1.97 | Br | 6-Br | H | iso-$C_3H_7$ | H | |
| 1.98 | Br | 6-Br | H | cyclo-$C_3H_5$ | H | |
| 1.99 | Br | 6-Br | H | $CH{=}CH_2$ | H | |
| 1.100 | Br | 6-Br | H | iso-$C_4H_9$ | H | |
| 1.101 | Br | 6-Br | H | $C{\equiv}CCH_3$ | H | |
| 1.102 | Br | 6-Br | H | $CH_3$ | $CH_3$ | |
| 1.103 | Br | 6-Br | H | $CH_3$ | $C_2H_5$ | |
| 1.104 | Br | 6-Br | H | H | $OCH_3$ | |
| 1.105 | Br | 6-Br | H | H | $OC_2H_5$ | |
| 1.106 | Br | 6-Br | H | $CH_3$ | $CH{=}CH_2$ | |
| 1.107 | Br | 6-Br | H | $CH_2-CH_2-CH_2$ | | |
| 1.108 | Br | 6-Br | H | $CH_2-CH_2-CH_2-CH_2$ | | |
| 1.109 | $CH_3$ | H | H | $CH_3$ | H | |
| 1.110 | $CH_3$ | H | H | $C_2H_5$ | H | |
| 1.111 | $CH_3$ | H | H | n-$C_3H_7$ | H | |
| 1.112 | $CH_3$ | H | H | iso-$C_3H_7$ | H | |
| 1.113 | $CH_3$ | H | H | cyclo-$C_3H_5$ | H | |
| 1.114 | $CH_3$ | H | H | n-$C_4H_9$ | H | |
| 1.115 | $CH_3$ | H | H | n-$C_6H_{13}$ | H | |
| 1.116 | $CH_3$ | H | H | iso-$C_4H_9$ | H | |
| 1.117 | $CH_3$ | H | H | sec-$C_4H_9$ | H | |
| 1.118 | $CH_3$ | H | H | $CH{=}CH_2$ | H | |
| 1.119 | $CH_3$ | H | H | $C{\equiv}CH$ | H | |
| 1.120 | $CH_3$ | H | H | $CH{=}C(CH_3)_2$ | H | |
| 1.121 | $CH_3$ | H | H | $CH_2C_6H_5$ | H | |
| 1.122 | $CH_3$ | H | H | $C_2H_4F$ | H | |
| 1.123 | $CH_3$ | H | $CH_3$ | $C_2H_5$ | H | |
| 1.124 | $CH_3$ | H | H | H | $OCH_3$ | |
| 1.125 | $CH_3$ | H | H | H | $OC_2H_5$ | |
| 1.126 | $CH_3$ | H | H | H | O-n-$C_3H_7$ | |
| 1.127 | $CH_3$ | H | H | cyclo-$C_3H_5$ | $CH_3$ | |
| 1.128 | $CH_3$ | H | H | $CH_3$ | $CH_3$ | |
| 1.129 | $CH_3$ | H | H | $CH_3$ | $C_2H_5$ | |
| 1.130 | $CH_3$ | H | H | $CH_3$ | iso-$C_3H_7$ | |
| 1.131 | $CH_3$ | H | H | $CH_3$ | $CH{=}CH_2$ | |
| 1.132 | $CH_3$ | H | H | $C_2H_5$ | $C_2H_5$ | |
| 1.133 | $CH_3$ | H | H | $CH_3$ | $C_6H_4Cl(4)$ | |
| 1.134 | $CH_3$ | H | H | $CH_3$ | $C_6H_5$ | |
| 1.135 | $CH_3$ | H | H | H | $C_6H_3Cl_2(2,4)$ | |
| 1.136 | $CH_3$ | H | H | $CH_2-CH_2-CH_2$ | | |
| 1.137 | $CH_3$ | H | H | $CH_2-CH_2-CH_2-CH_2$ | | |
| 1.138 | Cl | 5-Cl | H | $CH_3$ | H | |
| 1.139 | Cl | 5-Cl | H | $C_2H_5$ | H | |
| 1.140 | Cl | 5-Cl | H | iso-$C_3H_7$ | H | |
| 1.141 | Cl | 5-Cl | H | n-$C_3H_7$ | H | |
| 1.142 | Cl | 5-Cl | H | cyclo-$C_3H_5$ | H | |
| 1.143 | Cl | 5-Cl | H | $CH{=}CH_2$ | H | |
| 1.144 | Cl | 5-Cl | H | $CH{=}CHBr$ | H | |
| 1.145 | Cl | 5-Cl | H | H | $OC_2H_5$ | |
| 1.146 | Cl | 5-Cl | H | $CH_3$ | $CH_3$ | |
| 1.147 | Cl | 5-Cl | H | $CH_3$ | $C_2H_5$ | |

TABLE 1-continued

| Comp. No. | $R_2$ | $R_3$ | $R_4$ | $R_5$ | $R_6$ | Physical data |
|---|---|---|---|---|---|---|
| 1.148 | Cl | 5-Cl | H | $CH_3$ | cyclo-$C_3H_5$ | |
| 1.149 | Cl | 5-Cl | H | $CH_2-CH_2-CH_2$ | | |
| 1.150 | Cl | 5-Cl | H | $CH_2-CH_2-CH_2-CH_2$ | | |
| 1.151 | Cl | 3-$CH_3$ | H | $CH_3$ | H | |
| 1.152 | Cl | 3-$CH_3$ | H | $C_2H_5$ | H | |
| 1.153 | Cl | 3-$CH_3$ | H | n-$C_3H_7$ | H | |
| 1.154 | Cl | 3-$CH_3$ | H | iso-$C_3H_7$ | H | |
| 1.155 | Cl | 3-$CH_3$ | H | cyclo-$C_3H_5$ | H | |
| 1.156 | Cl | 3-$CH_3$ | H | $CH=CH_2$ | H | |
| 1.157 | Cl | 3-$CH_3$ | H | $CH=CHCH_3$ | H | |
| 1.158 | Cl | 3-$CH_3$ | H | $CH_2-CH_2-CH_2$ | | |
| 1.159 | Cl | 3-$CH_3$ | H | $CH_3$ | $CH_3$ | |
| 1.160 | Cl | 3-$CH_3$ | H | $CH_3$ | $C_2H_5$ | |
| 1.161 | Cl | 3-$CH_3$ | H | cyclo-$C_3H_5$ | $CH_3$ | |
| 1.162 | Br | 5-$CH_3$ | H | $C_2H_5$ | H | |
| 1.163 | Br | 5-$CH_3$ | H | n-$C_3H_7$ | H | |
| 1.164 | Br | 5-$CH_3$ | H | $C_6H_4CF_3(3)$ | H | |

TABLE 2

| No. | $R_1$ | $R_2$ | $R_5$ | $R_6$ | Physical data |
|---|---|---|---|---|---|
| 2.1 | $C_2H_5CH(CH_3)S$ | Cl | $C_2H_5$ | H | |
| 2.2 | $C_2H_5CH(CH_3)S$ | Cl | n-$C_3H_7$ | H | |
| 2.3 | $C_2H_5CH(CH_3)S$ | Cl | cyclo-$C_3H_5$ | H | |
| 2.4 | $(CH_3)_2CHCH_2SCH_2$ | Cl | $C_2H_5$ | H | |
| 2.5 | $(CH_3)_2CHCH_2SCH_2$ | Cl | n-$C_3H_7$ | H | |
| 2.6 | $(CH_3)_2C=CHCH_2O$ | Cl | $C_2H_5$ | H | |
| 2.7 | $(CH_3)_2C=CHCH_2O$ | Cl | n-$C_3H_7$ | H | |
| 2.8 | $(CH_3)_2C=CHCH_2O$ | Cl | $CH_3$ | $CH_3$ | |
| 2.9 | $C_2H_5(CH_3)C=CHCH_2O$ | Cl | $C_2H_5$ | H | |
| 2.10 | $C_2H_5(CH_3)C=CHCH_2O$ | Cl | n-$C_3H_7$ | H | |
| 2.11 | $C_2H_5(CH_3)C=CHCH_2O$ | Cl | iso-$C_3H_7$ | H | |
| 2.12 | $CH_3OCH(C_2H_5)CH_2O$ | Cl | cyclo-$C_3H_5$ | H | |
| 2.13 | $CH_3OCH(C_2H_5)CH_2O$ | Cl | $C_2H_5$ | H | |
| 2.14 | $C_2H_5OCH(C_2H_5)CH_2O$ | Br | $C_2H_5$ | H | |
| 2.15 | $C_2H_5OCH(C_2H_5)CH_2O$ | Br | n-$C_3H_7$ | H | |
| 2.16 | $C_2H_5OCH(C_2H_5)CH_2O$ | $CH_3$ | $C_2H_5$ | H | |
| 2.17 | $C_2H_5OCH(C_2H_5)CH_2O$ | $CH_3$ | n-$C_3H_7$ | H | |
| 2.18 | $CH_2=CHCH_2OCH_2$ | Cl | $C_2H_5$ | H | |
| 2.19 | $CH_2=CHCH_2OCH_2$ | Cl | n-$C_3H_7$ | H | |
| 2.20 | $CH_3CH=CHCH_2OCH_2$ | Cl | $C_2H_5$ | H | |
| 2.21 | $CH_3CH=CHCH_2OCH_2$ | Cl | n-$C_3H_7$ | H | |
| 2.22 | $(CH_3)_2C=CHCH_2OCH_2$ | Cl | $C_2H_5$ | H | |
| 2.23 | $(CH_3)_2C=CHCH_2OCH_2$ | Cl | n-$C_3H_7$ | H | |
| 2.24 | $HC\equiv CCH_2O$ | Cl | $C_2H_5$ | H | |
| 2.24A | $HC\equiv CCH_2O$ | Cl | $C_2H_5$ | H | $n_D^{20}$:1.5319 |
| 2.24B | $HC\equiv CCH_2O$ | Cl | $C_2H_5$ | H | $n_D^{20}$:1.5328 |
| 2.25 | $HC\equiv CCH_2O$ | Cl | n-$C_3H_7$ | H | |
| 2.25A | $HC\equiv CCH_2O$ | Cl | n-$C_3H_7$ | H | $n_D^{20}$:1.5266 |

TABLE 2-continued

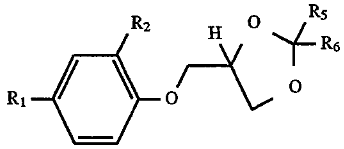

| No. | $R_1$ | $R_2$ | $R_5$ | $R_6$ | Physical data |
|---|---|---|---|---|---|
| 2.25B | $HC\equiv CCH_2O$ | Cl | n-$C_3H_7$ | H | $n_D^{20}$:1.5279 |
| 2.26 | $HC\equiv CCH_2O$ | Cl | $CH=CH_2$ | H | |
| 2.27 | $CH_3C\equiv CCH_2O$ | Cl | $C_2H_5$ | H | |
| 2.28 | $CH_3C\equiv CCH_2O$ | Cl | n-$C_3H_7$ | H | |
| 2.29 | $CH_3C\equiv CCH_2O$ | Cl | $CH=CH_2$ | H | |
| 2.30 | $C_2H_5C\equiv CCH_2O$ | Cl | $C_2H_5$ | H | |
| 2.31 | $C_2H_5C\equiv CCH_2O$ | Cl | n-$C_3H_7$ | H | |
| 2.32 | $ClHC=CHCH_2OCH_2$ | Cl | $C_2H_5$ | H | |
| 2.33 | $ClHC=CHCH_2OCH_2$ | Cl | n-$C_3H_7$ | H | |
| 2.34 | $H_2C=C(Cl)CH_2OCH_2$ | Cl | $C_2H_5$ | H | |
| 2.35 | $H_2C=C(Cl)CH_2OCH_2$ | Cl | n-$C_3H_7$ | H | |
| 2.36 | $H_2C=C(Cl)CH_2O$ | $CH_3$ | $C_2H_5$ | H | |
| 2.37 | $H_2C=C(Cl)CH_2O$ | $CH_3$ | n-$C_3H_7$ | H | |
| 2.38 | $Cl_2C=CHCH_2O$ | Br | $C_2H_5$ | H | |
| 2.39 | $Cl_2C=CHCH_2O$ | Br | n-$C_3H_7$ | H | |
| 2.40 | $BrC\equiv CCH_2O$ | Cl | $C_2H_5$ | H | |
| 2.41 | $BrC\equiv CCH_2O$ | Cl | n-$C_3H_7$ | H | |
| 2.42 | $BrC\equiv CCH_2O$ | Cl | cyclo-$C_3H_5$ | H | |
| 2.43 | $BrC\equiv CCH_2OCH_2$ | $CH_3$ | $C_2H_5$ | H | |
| 2.44 | $BrC\equiv CCH_2OCH_2$ | $CH_3$ | n-$C_3H_7$ | H | |
| 2.45 | cyclohexyl | Cl | $C_2H_5$ | H | |
| 2.46 | cyclopentyl-O | Cl | $C_2H_5$ | H | |
| 2.47 | cyclohexyl-O | Cl | $C_2H_5$ | H | |
| 2.48 | cyclohexyl-O | Cl | n-$C_3H_7$ | H | |
| 2.49 | cyclopentyl-$OCH_2$ | Cl | $C_2H_5$ | H | |
| 2.50 | cyclopentyl-$OCH_2$ | Cl | n-$C_3H_7$ | H | |
| 2.51 | cyclohexyl-$OCH_2$ | Cl | $C_2H_5$ | H | |
| 2.52 | cyclohexyl-$OCH_2$ | Cl | n-$C_3H_7$ | H | |
| 2.53 | $C_2H_5C\equiv CCH_2$ | Br | $C_2H_5$ | H | |
| 2.54 | $C_2H_5C\equiv C$ | Br | $C_2H_5$ | H | |
| 2.55 | $HC\equiv CCH_2CH_2CH_2O$ | Cl | $C_2H_5$ | H | |
| 2.56 | $HC\equiv CCH_2CH_2CH_2O$ | Br | $C_2H_5$ | H | |
| 2.57 | $C_2H_5OC_2H_4O$ | Cl | $C_2H_5$ | H | |
| 2.58 | $C_2H_5OC_2H_4O$ | Cl | n-$C_3H_7$ | H | |
| 2.59 | $C_2H_5SC_2H_4O$ | Cl | $C_2H_5$ | H | |
| 2.60 | $C_2H_5SC_2H_4O$ | Cl | n-$C_3H_7$ | H | |
| 2.61 | iso-$C_3H_7-SC_2H_4S$ | Cl | $C_2H_5$ | H | |
| 2.62 | $C_2H_5CH(CH_3)CH_2$ | Cl | $C_2H_5$ | H | |
| 2.63 | $C_2H_5CH(CH_3)CH_2$ | Cl | n-$C_3H_7$ | H | |
| 2.64 | $C_2H_5CH(CH_3)CH_2$ | Cl | cyclo-$C_3H_5$ | H | |
| 2.65 | $H_2C=C(CH_3)CH_2O$ | Cl | $C_2H_5$ | H | |
| 2.66 | $H_2C=C(CH_3)CH_2O$ | Cl | n-$C_3H_7$ | H | |
| 2.67 | $ClCH_2CH_2CH_2O$ | Cl | $C_2H_5$ | H | |
| 2.68 | $ClCH_2CH_2CH_2O$ | Cl | n-$C_3H_7$ | H | |
| 2.69 | $BrCH_2CH_2CH_2O$ | Cl | $C_2H_5$ | H | |
| 2.70 | $BrCH_2CH_2CH_2O$ | Cl | n-$C_3H_7$ | H | |
| 2.71 | $(C_2H_5)_2CHO$ | Cl | $C_2H_5$ | H | |
| 2.72 | $(C_2H_5)_2CHO$ | Cl | n-$C_3H_7$ | H | |
| 2.73 | $CH_3CH(CH_3)CH_2CH_2CH_2$ | Cl | $C_2H_5$ | H | |
| 2.74 | $CH_3CH(CH_3)CH_2CH_2CH_2$ | Cl | n-$C_3H_7$ | H | |
| 2.75 | sec-$C_4H_9$ | Cl | $C_2H_5$ | H | |
| 2.76 | sec-$C_4H_9$ | Cl | n-$C_3H_7$ | H | |
| 2.77 | $C_2H_5(CH_3)_2C$ | Cl | $C_2H_5$ | H | |
| 2.78 | $C_2H_5(CH_3)_2C$ | Cl | n-$C_3H_7$ | H | |

TABLE 2-continued

| No. | $R_1$ | $R_2$ | $R_5$ | $R_6$ | Physical data |
|---|---|---|---|---|---|
| 2.79 | n-$C_6H_{13}$ | Cl | $C_2H_5$ | H | |
| 2.80 | n-$C_6H_{13}$ | Cl | n-$C_3H_7$ | H | |
| 2.81 | n-$C_4H_9$ | Cl | $C_2H_5$ | H | |
| 2.82 | n-$C_4H_9$ | Cl | n-$C_3H_7$ | H | |
| 2.83 | n-$C_3H_7(CH_3)CH$ | Cl | $C_2H_5$ | H | |
| 2.84 | n-$C_3H_7(CH_3)CH$ | Cl | n-$C_3H_7$ | H | |
| 2.85 | n-$C_4H_9(CH_3)CH$ | Cl | $C_2H_5$ | H | |
| 2.86 | n-$C_4H_9(CH_3)CH$ | Cl | n-$C_3H_7$ | H | |
| 2.87 | $C_2H_5OCH_2$ | Cl | $C_2H_5$ | H | |
| 2.88 | $C_2H_5OCH_2$ | Cl | n-$C_3H_7$ | H | |
| 2.89 | n-$C_3H_7CH(CH_3)O$ | Cl | $C_2H_5$ | H | |
| 2.90 | n-$C_3H_7CH(CH_3)O$ | Cl | n-$C_3H_7$ | H | |
| 2.91 | $(CH_3)_2CHCH_2O$ | Cl | $C_2H_5$ | H | |
| 2.92 | $(CH_3)_2CHCH_2O$ | Cl | n-$C_3H_7$ | H | |
| 2.93 | $(CH_3)_2CHCH_2O(CH_3)CH$ | Cl | $C_2H_5$ | H | |
| 2.94 | $(CH_3)_2CHCH_2O(CH_3)CH$ | Cl | n-$C_3H_7$ | H | |
| 2.95 | $(CH_3)_3CO$ | Cl | $C_2H_5$ | H | |
| 2.96 | $(CH_3)_3CO$ | Cl | n-$C_3H_7$ | H | |
| 2.97 | $C_8H_{17}O$ | Cl | $C_2H_5$ | H | |
| 2.98 | $C_8H_{17}O$ | Cl | n-$C_3H_7$ | H | |
| 2.99 | $(CH_3)_2CHCH(CH_3)O$ | Cl | $C_2H_5$ | H | |
| 2.100 | $(CH_3)_2CHCH(CH_3)O$ | Cl | n-$C_3H_7$ | H | |
| 2.101 | $CH_3OCH(CH_3)O$ | Cl | $C_2H_5$ | H | |
| 2.102 | $CH_3OCH(CH_3)O$ | Cl | n-$C_3H_7$ | H | |
| 2.103 | n-$C_3H_7OCH_2$ | Cl | $C_2H_5$ | H | |
| 2.104 | n-$C_3H_7OCH_2$ | Cl | n-$C_3H_7$ | H | |
| 2.105 | $C_2H_5OCH(C_2H_5)CH_2$ | Cl | $C_2H_5$ | H | |
| 2.106 | $C_2H_5OCH(C_2H_5)CH_2$ | Cl | n-$C_3H_7$ | H | |
| 2.107 | $HC\equiv CCH_2O$ | Cl | i-$C_3H_7$ | H | |
| 2.107A | $HC\equiv CCH_2O$ | Cl | i-$C_3H_7$ | H | $n_D^{20}$:1.5268 |
| 2.107B | $HC\equiv CCH_2O$ | Cl | i-$C_3H_7$ | H | $n_D^{20}$:1.5271 |
| 2.108 | $HC\equiv CCH_2O$ | Cl | cyclo-$C_3H_5$ | H | |
| 2.108A | $HC\equiv CCH_2O$ | Cl | cyclo-$C_3H_5$ | H | $n_D^{20}$:1.5451 |
| 2.108B | $HC\equiv CCH_2O$ | Cl | cyclo-$C_3H_5$ | H | $n_D^{20}$:1.5460 |

TABLE 3

| Comp. No. | $R_2$ | $R_4$ | $R_5$ | $R_6$ | Physical data |
|---|---|---|---|---|---|
| 3.1 | Cl | H | H | $C_2H_5$ | |
| 3.1A | Cl | H | H | $C_2H_5$ | $n_D^{20}$:1.5035 |
| 3.1B | Cl | H | H | $C_2H_5$ | $n_D^{20}$:1.5043 |
| 3.2 | Cl | H | H | n-$C_3H_7$ | |
| 3.2A | Cl | H | H | n-$C_3H_7$ | $n_D^{20}$:1.5009 |
| 3.2B | Cl | H | H | n-$C_3H_7$ | $n_D^{20}$:1.5020 |
| 3.3 | Br | H | H | $C_2H_5$ | |
| 3.4 | Cl | H | H | $OCH_3$ | |
| 3.5 | Cl | H | H | $OC_2H_5$ | |
| 3.6 | Cl | H | $CH_3$ | H | |
| 3.7 | Cl | H | $C_2H_5$ | H | |
| 3.8 | Cl | H | n-$C_3H_7$ | H | |

TABLE 3-continued

| Comp. No. | $R_2$ | $R_4$ | $R_5$ | $R_6$ | Physical data |
|---|---|---|---|---|---|
| 3.9 | Cl | H | iso-$C_3H_7$ | H | |
| 3.10 | Cl | H | cyclo-$C_3H_5$ | H | |
| 3.10A | Cl | H | cyclo-$C_3H_5$ | H | $n_D^{20}$:1.5139 |
| 3.10B | Cl | H | cyclo-$C_3H_5$ | H | $n_D^{20}$:1.5151 |
| 3.11 | Cl | H | cyclo-$C_3H_5$ | $CH_3$ | |
| 3.12 | Cl | H | iso-$C_4H_9$ | H | |
| 3.13 | Cl | H | $CH=CH_2$ | H | |
| 3.14 | Cl | H | $CH=CHCH_3$ | H | |
| 3.15 | Cl | H | $C\equiv CH$ | H | |
| 3.16 | Cl | H | $CH_3$ | $CH_3$ | |
| 3.17 | Cl | H | $CH_3$ | $C_2H_5$ | |

TABLE 3-continued

| Comp. No. | $R_2$ | $R_4$ | $R_5$ | $R_6$ | Physical data |
|---|---|---|---|---|---|
| 3.18 | Cl | H | $CH_3$ | $CH=CH_2$ | |
| 3.19 | Cl | H | $C_2H_5$ | $C_2H_5$ | |
| 3.20 | Cl | H | H | $C_6H_4Cl(4)$ | |
| 3.21 | Cl | H | H | $C_6H_3Cl_2(2,4)$ | |
| 3.22 | Cl | H | H | $C_6H_4C_2H_5(4)$ | |
| 3.23 | Cl | H | $CH_2CH_2CH_2$ | | |
| 3.24 | Cl | H | $CH_2CH_2CH_2CH_2$ | | |
| 3.25 | Cl | H | H | cyclo-$C_5H_9$ | |
| 3.26 | Cl | $CH_3$ | $C_2H_5$ | H | |
| 3.27 | Br | H | H | $OC_2H_5$ | |
| 3.28 | Br | H | $CH_3$ | H | |
| 3.29 | Br | H | $C_2H_5$ | H | |
| 3.30 | Br | H | n-$C_3H_7$ | H | |
| 3.31 | Br | H | iso-$C_3H_7$ | H | |
| 3.32 | Br | H | cyclo-$C_3H_5$ | H | |
| 3.33 | Br | H | $CH=CH_2$ | H | |
| 3.34 | Br | H | $CH_3$ | $CH_3$ | |
| 3.35 | Br | H | $CH_3$ | $C_2H_5$ | |
| 3.36 | Br | H | $CH_2CH_2CH_2$ | | |
| 3.37 | Br | H | $CH_2CH_2CH_2CH_2$ | | |
| 3.38 | Br | H | $CH_2CH_2CH_2CH_2CH_2$ | | |
| 3.39 | Br | H | $CH_2C_6H_4Cl(4)$ | H | |
| 3.40 | $CH_3$ | H | H | $OC_2H_5$ | |
| 3.41 | $CH_3$ | H | H | $OCH_3$ | |
| 3.42 | $CH_3$ | H | $CH_3$ | H | |
| 3.43 | $CH_3$ | H | $C_2H_5$ | H | |
| 3.44 | $CH_3$ | H | n-$C_3H_7$ | H | |
| 3.45 | $CH_3$ | H | iso-$C_3H_7$ | H | |
| 3.46 | $CH_3$ | H | 2-ethylhexyl | H | |
| 3.47 | $CH_3$ | H | cyclo-$C_3H_5$ | $CH_3$ | |
| 3.48 | $CH_3$ | H | $CH_2CH_2CH_2$ | | |
| 3.49 | $CH_3$ | H | $CH_2CH_2CH_2CH_2$ | | |
| 3.50 | $CH_3$ | H | H | $C_6H_4Cl(4)$ | |
| 3.51 | $CH_3$ | H | H | $C_6H_3F_2(2,6)$ | |
| 3.52 | $CH_3$ | H | H | $C_6H_3Cl_2(2,6)$ | |

TABLE 4

| Comp. No. | $R_2$ | $R_4$ | $R_5$ | $R_6$ | Physical data |
|---|---|---|---|---|---|
| 4.1 | Cl | H | $CH_3$ | H | |
| 4.2 | Cl | H | $C_2H_5$ | H | |
| 4.2A | Cl | H | $C_2H_5$ | H | $n_D^{20}$:1.5080 |
| 4.2B | Cl | H | $C_2H_5$ | H | $n_D^{20}$:1.5089 |
| 4.3 | Cl | H | n-$C_3H_7$ | H | |
| 4.4 | Cl | H | iso-$C_3H_7$ | H | |
| 4.5 | Cl | H | cyclo-$C_3H_5$ | H | |
| 4.6 | Cl | H | iso-$C_4H_9$ | H | |
| 4.7 | Cl | H | $CH=CH_2$ | H | |
| 4.8 | Cl | H | $C\equiv CH$ | H | |
| 4.9 | Cl | H | H | $OCH_3$ | |
| 4.10 | Cl | H | H | $OC_2H_5$ | |
| 4.11 | Cl | H | $CH_3$ | $CH_3$ | |
| 4.12 | Cl | H | $CH_3$ | $C_2H_5$ | |
| 4.13 | Cl | H | $CH_3$ | $CH=CH_2$ | |
| 4.14 | Cl | H | $C_2H_5$ | $C_2H_5$ | |

TABLE 4-continued

| Comp. No. | $R_2$ | $R_4$ | $R_5$ | $R_6$ | Physical data |
|---|---|---|---|---|---|
| 4.15 | Cl | H | H | $C_6H_4Cl(4)$ | |
| 4.16 | Cl | H | H | $C_6H_3Cl_2(2,4)$ | |
| 4.17 | Cl | H | H | $C_6H_4CH_3(4)$ | |
| 4.18 | Cl | H | $CH_2CH_2CH_2$ | | |
| 4.19 | Cl | H | $CH_2CH_2CH_2CH_2$ | | |
| 4.20 | Br | H | $C_2H_5$ | H | |
| 4.21 | Br | H | n-$C_3H_7$ | H | |
| 4.22 | Br | H | iso-$C_3H_7$ | H | |
| 4.23 | Br | H | cyclo-$C_3H_5$ | H | |
| 4.24 | Br | H | $CH{=}CH_2$ | H | |
| 4.25 | Br | H | $CH{=}CHCH_3$ | H | |
| 4.26 | Br | H | H | $OCH_2H_5$ | |
| 4.27 | Br | H | $CH_3$ | $CH{=}CH_2$ | |
| 4.28 | Br | H | $CH_3$ | $C_2H_5$ | |
| 4.29 | $CH_3$ | H | $CH_3$ | H | |
| 4.30 | $CH_3$ | H | $C_2H_5$ | H | |
| 4.31 | $CH_3$ | H | n-$C_3H_7$ | H | |
| 4.32 | $CH_3$ | H | iso-$C_3H_7$ | H | |
| 4.33 | $CH_3$ | H | cyclo-$C_3H_5$ | H | |
| 4.34 | $CH_3$ | H | iso-$C_4H_9$ | H | |
| 4.35 | $CH_3$ | H | $CH{=}CH_2$ | H | |
| 4.36 | $CH_3$ | H | $C{=}CH$ | H | |
| 4.37 | $CH_3$ | H | H | $CH_3$ | |
| 4.38 | $CH_3$ | H | H | $OC_2H_5$ | |
| 4.39 | $CH_3$ | H | $CH_3$ | $CH_3$ | |
| 4.40 | $CH_3$ | H | $CH_3$ | $C_2H_5$ | |
| 4.41 | $CH_3$ | H | $CH_2CH_2CH_2$ | | |
| 4.42 | $CH_3$ | H | $CH_2CH_2CH_2CH_2$ | | |
| 4.43 | $CH_3$ | H | $CH_2CH_2CH_2CH_2CH_2$ | | |
| 4.44 | $CH_3$ | H | H | cyclohexyl | |
| 4.45 | $CH_3$ | H | $CH_3$ | $CH{=}CH_2$ | |
| 4.46 | $CH_3$ | $CH_3$ | $C_2H_5$ | H | |

TABLE 5

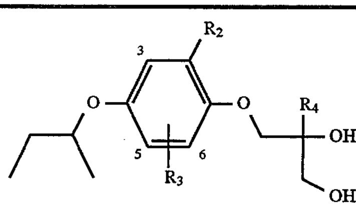

| Comp. No. | $R_2$ | $R_3$ | $R_4$ | Physical data |
|---|---|---|---|---|
| 5.1 | Cl | H | H | $n_D^{20}$:1.5329 |
| 5.2 | Br | H | H | $n_D^{20}$:1.5481 |
| 5.3 | Br | 6-Br | H | $n_D^{20}$:1.5667 |
| 5.4 | Cl | H | $CH_3$ | |
| 5.5 | F | H | H | |
| 5.6 | Br | H | $CH_3$ | |
| 5.7 | $CH_3$ | H | H | |
| 5.8 | $CH_3$ | H | $CH_3$ | |
| 5.9 | Cl | 5-Cl | H | |
| 5.10 | Cl | 3-$CH_3$ | H | |
| 5.11 | Br | 5-$CH_3$ | H | |

TABLE 6

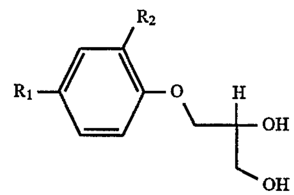

| Comp. No. | $R_1$ | $R_2$ | Physical data |
|---|---|---|---|
| 6.1 | $C_2H_5CH(CH_3)S$ | Cl | |
| 6.2 | $(CH_3)_2CHCH_2SCH_2$ | Cl | |
| 6.3 | $(CH_3)_2C{=}CHCH_2O$ | Cl | |
| 6.4 | $C_2H_5(CH_3)C{=}CHCH_2O$ | Cl | |
| 6.5 | $CH_3OCH(C_2H_5)CH_2O$ | Cl | |
| 6.6 | $C_2H_5OCH(C_2H_5)CH_2O$ | Br | |
| 6.7 | $C_2H_5OCH(C_2H_5)CH_2O$ | $CH_3$ | |
| 6.8 | $CH_2{=}CHCH_2OCH_2$ | Cl | |
| 6.9 | $CH_3CH{=}CHCH_2OCH_2$ | Cl | |
| 6.10 | $(CH_3)_2C{=}CHCH_2OCH_2$ | Cl | |
| 6.11 | $HC{\equiv}CCH_2O$ | Cl | m.p.:85–86° |

TABLE 6-continued

| Comp. No. | $R_1$ | $R_2$ | Physical data |
|---|---|---|---|
| 6.12 | $CH_3C{\equiv}CCH_2O$ | Cl | |
| 6.13 | $C_2H_5C{\equiv}CCH_2O$ | Cl | |
| 6.14 | $Cl(H)C{=}CHCH_2OCH_2$ | Cl | |
| 6.15 | $H_2C{=}C(Cl)CH_2OCH_2$ | Cl | |
| 6.16 | $H_2C{=}C(Cl)CH_2O$ | $CH_3$ | |
| 6.17 | $Cl_2C{=}CHCH_2O$ | Br | |
| 6.18 | $BrC{=}CCH_2O$ | Cl | |
| 6.19 | $BrC{=}CCH_2OCH_2$ | $CH_3$ | |
| 6.20 | cyclohexyl | Cl | |
| 6.21 | cyclopentyl-O | Cl | |
| 6.22 | cyclohexyl-O | Cl | |
| 6.23 | cyclopentyl-$OCH_2$ | Cl | |
| 6.24 | cyclohexyl-$OCH_2$ | Cl | |
| 6.25 | $C_2H_5C{\equiv}CCH_2$ | Br | |
| 6.26 | $C_2H_5C{\equiv}C$ | Br | |
| 6.27 | $HC{\equiv}CCH_2CH_2CH_2O$ | Cl | |
| 6.28 | $HC{\equiv}CCH_2CH_2CH_2O$ | Br | |
| 6.29 | $C_2H_5OC_2H_4O$ | Cl | |
| 6.30 | $C_2H_5SC_2H_4O$ | Cl | |
| 6.31 | iso-$C_3H_7SC_2H_4S$ | Cl | |
| 6.32 | $C_2H_4SCH(CH_3)CH_2$ | Cl | |
| 6.33 | $H_2C{=}C(CH_3)CH_2O$ | Cl | |
| 6.34 | $ClCH_2CH_2CH_2O$ | Cl | |
| 6.35 | $BrCH_2CH_2CH_2O$ | Cl | |
| 6.36 | $(C_2H_5)_2CHO$ | Cl | |
| 6.37 | $CH_3CH(CH_3)CH_2CH_2CH_2$ | Cl | |
| 6.38 | sec-$C_4H_9$ | Cl | |
| 6.39 | $C_2H_5C(CH_3)_2$ | Cl | |
| 6.40 | n-$C_6H_{13}$ | Cl | |
| 6.41 | n-$C_4H_9$ | Cl | |
| 6.42 | n-$C_3H_7(CH_3)CH$ | Cl | |
| 6.43 | n-$C_4H_9(CH_3)CH$ | Cl | |
| 6.44 | $C_2H_5OCH_2$ | Cl | |
| 6.45 | n-$C_3H_7CH(CH_3)O$ | Cl | |
| 6.46 | $(CH_3)_2CHCH_2O$ | Cl | |
| 6.47 | $(CH_3)_2CHCH_2O(CH_3)CH$ | Cl | |
| 6.48 | $(CH_3)_3CO$ | Cl | |
| 6.49 | $C_8H_{17}O$ | Cl | |
| 6.50 | $(CH_3)_2CHCH(CH_3)O$ | Cl | |
| 6.51 | $CH_3OCH(CH_3)O$ | Cl | |
| 6.52 | n-$C_3H_7OCH_2$ | Cl | |
| 6.53 | $C_2H_5OCH(C_2H_5)CH_2$ | Cl | |

TABLE 7

| Comp. No. | $R_2$ | $R_4$ | Physical data |
|---|---|---|---|
| 7.1 | Cl | H | $n_D^{20}$:1.5251 |
| 7.2 | Br | H | |
| 7.3 | Cl | $CH_3$ | |
| 7.4 | $CH_3$ | H | |

TABLE 8

| Comp. No. | $R_2$ | $R_4$ | Physical data |
|---|---|---|---|
| 8.1 | Cl | H | |
| 8.2 | Br | H | |
| 8.3 | $CH_3$ | H | |
| 8.4 | $CH_3$ | $CH_3$ | |

Formulation Examples (% = percent by weight)

| Example F1: Emulsion concentrates | a) | b) | c) |
|---|---|---|---|
| Active ingedient | 25% | 40% | 50% |
| Calcium dodecylbenzenesulfonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing finely ground active ingredient and additives results in an emulsion concentrate which, when diluted with water, gives emulsions of the desired concentration.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol (MW 400) | — | 70% | — | — |
| N-Methylpyrrolid-2-one | 20% | — | — | — |
| Epoxidized coconut oil | — | — | 1% | 5% |
| Petroleum ether (boiling range: 160-190°) | — | — | 94% | — |

Mixing finely ground active ingredient and additives results in a solution which is suitable for use in the form of microdrops.

| Example F3: Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier mixture, and the solvent is evaporated in vacuo.

| Example F4: Dusts | a) | b) |
|---|---|---|
| Active ingredient | 2% | 5% |
| Highly disperse silica | 1% | 5% |
| Talc | 97% | — |
| Kaolin | — | 90% |

Mixing active ingredient and carriers gives ready-to-use dusts.

| Example F5: Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7–8 mol of EO) | — | 2% | — |
| Highly disperse silica | 5% | 10% | 10% |
| Kaolin | 62% | 27% | — |

Active ingredient and additives are mixed, and the mixture is ground in a suitable mill. This gives wettable powders which can be diluted with water to give suspensions of the desired concentration.

| Example F6: Emulsion concentrate | |
|---|---|
| Active ingredient | 10% |
| Octylphenol polyethylene glycol ether (4–5 mol of EO) | 3% |
| Calcium dodecylbenzenesulfonate | 3% |
| Castor oil polyethylene glycol ether (36 mol of EO) | 4% |
| Cyclohexanone | 30% |
| Xylene mixture | 50% |

Mixing finely ground active ingredient and additives gives an emulsion concentrate which, when diluted with water, gives emulsions of the desired concentration.

| Example F7: Dusts | a) | b) |
|---|---|---|
| Active ingredient | 5% | 8% |
| Talc | 95% | — |
| Kaolin | — | 92% |

Ready-to-use dusts are obtained by mixing active ingredient and carrier and grinding the mixture in a suitable mill.

| Example F8: Extruder granules | |
|---|---|
| Active ingredient | 10% |
| Sodium lignosulfonate | 2% |
| Carboxymethylcellulose | 1% |
| Kaolin | 87% |

Active ingredient and additives are mixed, the mixture is ground, moistened with water, extruded and granulated, and the granules are dried in a stream of air.

| Example F9: Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin which has been moistened with polyethylene glycol, resulting in dust-free coated granules.

| Example F10: Suspension concentrate | |
|---|---|
| Active ingredient | 40% |
| Ethylene glycol | 10% |
| Nonylphenol polyethylene glycol ether (15 mol of EO) | 6% |
| Sodium lignosulfonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing finely ground active ingredient and additives gives a suspension concentrate which, when diluted with water, results in suspensions of the desired concentration.

Biological Examples:

Example B1: Action against *Boophilus microplus*

Adult ticks (females) which have sucked themselves full are attached to a PVC sheet and covered with a cotton wool ball. As the treatment, 10 ml of an aqueous test solution comprising 125 ppm of the active ingredient to be tested are poured over the test animals. The cotton wool ball is then removed, and the ticks are incubated for oviposition over a period of 4 weeks. The action against *Boophilus microplus* becomes apparent either in the form of mortality or sterility in the case of the females or as an ovicidal action in the case of the eggs.

In this test, a good activity is exhibited by compounds of Tables 1 to 4. The compounds No. 1.1A, 1.1B, 1.2A and 1.2B, in particular, have an activity of over 80%.

Example B2: Ovicidal action against *Cydia pomonella*

Eggs of *Cydia pomonella* which have been laid on filter paper are briefly immersed into a test solution comprising 400 ppm of the active ingredient to be tested in acetone/water. After the test solution has dried on, the eggs are incubated in Petri dishes. After 6 days, the percentage hatching rate of the eggs is evaluated in comparison with untreated control batches (% reduction in hatching rate).

In this test, a good activity is exhibited by compounds of Tables 1 to 4. The compounds No. 1.1A, 1.1B, 1.2A and 1.2B, in particular, have an activity of over 80%.

Example B3: Ovicidal action against *Adoxophyes reticulana*

Eggs of *Adoxophyes reticulana* which have been laid on filter paper are briefly immersed into a test solution comprising 400 ppm of the active ingredient to be tested in acetone/water. After the test solution has dried on, the eggs are incubated in Petri dishes. After 6 days, the percentage hatching rate of the eggs is evaluated in comparison with untreated control batches (% reduction in hatching rate).

In this test, a good activity is exhibited by compounds of Tables 1 to 4. The compounds No. 1.1A, 1.1B, 1.2A and 1.2B, in particular, have an activity of over 80%.

Example B4: Ovicidal action against *Lobesia botrana*

Eggs of *Lobesia botrana* which have been laid on filter paper are briefly immersed into a test solution comprising 400 ppm of the active ingredient to be tested in acetone/water. After the test solution has dried on, the eggs are incubated in Petri dishes. After 6 days, the percentage hatching rate of the eggs is evaluated in comparison with untreated control batches (% reduction in hatching rate).

In this test, a good activity is exhibited by compounds of Tables 1 to 4.

Example B5: Action against *Aonidiella aurantii*

Potato tubers are populated with crawlers of *Aonidiella aurantii* (armoured scales). After approximately 2 weeks, the potatoes are immersed into an aqueous spray mixture made with an emulsion or suspension and comprising the active ingredient to be tested in a concentration of 400 ppm. After the potato tubers which have been treated in this manner have dried, they are incubated in a plastic container. As the evaluation 10–12 weeks later, the survival rate of the crawlers of the first subsequent generation of the treated scale insect population is compared with the survival rate of the untreated control batches. In this test, compounds of Tables 1 to 4 exhibit good activity.

Example B6: Action against *Nilaparvata lugens*

Rice plants are treated with an aqueous emulsion spray mixture, comprising 400 ppm of the active ingredient. After the spray coating has dried on, the rice plants are populated with plant hopper larvae of the 2nd and 3rd instar. 21 days later, the test is evaluated. The percentage reduction in population (% action) is determined by comparing the number of surviving plant hoppers on the treated plants with those on the untreated plants. In this test, a good activity is exhibited by compounds of Tables 1 to 4. The compounds No. 1.1A, 1.1B, 1.2A and 1.2B, in particular, have an activity of over 80%.

Example B7: Action against *Nephotettix cincticeps*

Rice plants are treated with an aqueous emulsion spray mixture, comprising 400 ppm of the active ingredient. After the spray coating has dried on, the rice plants are populated with leaf hopper larvae of the 2nd and 3rd instar. 21 days later, the test is evaluated. The percentage reduction in population (% action) is determined by comparing the number of surviving leaf hoppers on the treated plants with those on the untreated plants.

In this test, a good activity is exhibited by compounds of Tables 1 to 4.

Example B8: Action against *Bemisia tabaci*

Dwarf bean plants are placed under gauze cages find populated with adults of *Bemisia tabaci* (whitefly). After oviposition has taken place, all adults are removed, and, 10 days later, the plants together with the nymphs thereon are treated with an aqueous emulsion spray mixture of the active ingredients to be tested (concentration 400 ppm). 14 days after application of the active ingredient, the test is evaluated for percentage hatching rate in comparison with the untreated control batches.

In this test, compounds of Tables 1 to 4 exhibit good activity.

Example B9: Action against *Tetranychus urticae*

Young bean plants are populated with a mixed population of *Tetranychus urticae* and, 1 day later, sprayed with an aqueous emulsion spray mixture comprising 400 ppm of the active ingredient. The plants are subsequently incubated for 6 days at 25° C. and then evaluated. The percentage reduction in the population (% action) is determined by comparing the number of dead eggs, larvae and adults on the treated plants with those on the untreated plants.

In this test, compounds of Tables 1 to 4 exhibit good activity.

Example B10: Ovicidal/larvicidal action against Hellothis virescens

Eggs of *Heliothis virescens* which have been laid on cotton are sprayed with an aqueous emulsion spray mixture comprising 400 ppm of the active ingredient. After 8 days, the percentage hatching rate of the eggs and the survival rate of the caterpillars are evaluated in comparison with untreated control batches (% reduction in population).

In this test, compounds of Tables 1 to 4 exhibit good activity.

Example B11: Action against *Panonychus ulmi* (OP- and carb.-resistant)

Apple seedlings are populated with adult females of *Panonychus ulmi*. After seven days, the infected plants are sprayed to drip point with an aqueous emulsion spray mixture comprising 400 ppm of the test compound and grown in a green-house. After 14 days, the test is evaluated. The percentage reduction in population (% action) is determined by comparing the number of dead spider mites on the treated plants with those on the untreated plants.

In this test, compounds of Tables 1 to 4 exhibit good activity.

Example B12: Action against *Ctenocephalides felis*

20 to 25 flea eggs are introduced into a horizontally positioned 50-ml tissue culture flask into which 15 g of flea larvae medium comprising 100 ppm of the active ingredient to be tested have previously been introduced. The test flasks are incubated in an incubator at 26° to 27° C. and an atmospheric humidity of 60–70%. After 21 days, they are checked for the presence of adult fleas, unhatched pupae and larvae.

In this test, compounds of Tables 1 to 4 exhibit good activity.

Example B13: Action against *Bemisia tabaci* eggs

Dwarf bean plants are placed under gauze cages and populated with adults of *Bemisia tabaci* (whitefly). After oviposition has taken place, all adults are removed, and, 2 days later, the plants together with the nymphs thereon are treated with an aqueous emulsion spray mixture of the active ingredients to be tested (concentration 400 ppm). 10 days after application of the active ingredient, the test is evaluated for percentage hatching rate in comparison with the untreated control batches.

In this test, compounds of Tables 1 to 4 exhibit good activity.

What is claimed is:

1. A compound of the formula in which $R_1$ is substituted or unsubstituted $C_1$–$C_8$alkyl, substituted or unsubstituted $C_3$–$C_8$cycloalkyl, substituted or unsubstituted $C_2$–$C_8$alkenyl, substituted or unsubstituted $C_2$–$C_8$alkynyl, substituted or unsubstituted $C_1$–$C_8$alkoxy, substituted or unsubstituted $C_3$–$C_8$cycloalkoxy, substituted or unsubstituted $C_2$–$C_8$alkenyloxy, substituted or unsubstituted $C_2$–$C_8$alkynyloxy or substituted or unsubstituted $C_1$–$C_8$alkylthio;

$R_2$ is chlorine or bromine;

$R_3$ is H, halogen or methyl;

$R_4$ is H or methyl;

$R_5$ is H, $C_1$–$C_8$alkyl, $C_3$–$C_6$cycloalkyl, $C_2$–$C_5$alkenyl, or $C_2$–$C_5$alkynyl; and $R_6$ is H, $C_1$–$C_6$alkyl.

2. A new compound according to claim 1, of the formula I in which $R_1$ is $C_1$–$C_8$alkyl, $C_3$–$C_8$cycloalkyl, $C_2$–$C_8$alkenyl, $C_2$–$C_8$alkynyl, $C_1$–$C_8$alkoxy, $C_3$–$C_8$cycloalkoxy, $C_2$–$C_8$alkoxy-$C_1$–$C_4$alkyl, $C_1$–$C_8$alkoxy-$C_2$–$C_4$alkoxy-$C_1$–$C_4$alkyl, $C_1$–$C_8$alkoxy-$C_2$–$C_4$alkoxy, $C_4$–$C_8$cycloalkoxy-$C_1$–$C_3$alkyl, $C_3$–$C_8$alkenyloxy, $C_3$–$C_8$alkenyloxy-$C_1$–$C_3$alkyl, $C_3$–$C_8$alkynyloxy, $C_3$–$C_8$alkynyloxy-$C_1$–$C_3$alkyl, $C_3$–$C_8$haloalkyl, $C_3$–$C_8$haloalkenyl, $C_3$–$C_8$haloalkynyl, $C_3$–$C_8$haloalkoxy, $C_3$–$C_8$haloalkoxy-$C_1$–$C_3$alkyl, $C_3$–$C_8$haloalkenyloxy, $C_3$–$C_8$haloalkenyloxy-$C_1$–$C_3$alkyl, $C_3$–$C_8$haloalkynyloxy, $C_3$–$C_8$haloalkynyloxy-$C_1$–$C_3$alkyl, $C_3$–$C_8$alkylthio, $C_3$–$C_8$alkylthio-$C_1$–$C_3$alkyl, $C_2$–$C_8$alkylthio-$C_2$–$C_3$alkoxy, $C_2$–$C_8$alkylthio-$C_2$–$C_3$alkoxy-$C_1$–$C_4$alkyl, or $C_2$–$C_8$alkylthio-$C_2$–$C_3$alkylthio, $C_2$–$C_8$alkylthio-$C_2$–$C_3$alkylthio-$C_1$–$C_4$alkyl, $C_2$–$C_8$alkoxy-$C_2$–$C_3$alkylthio or $C_2$–$C_8$alkoxy-$C_2$–$C_3$alkylthio-$C_1$–$C_4$alkyl;

$R_2$ is chlorine or bromine;

$R_3$ is H, halogen or methyl;

$R_4$ is H or methyl;

$R_5$ is H, $C_1$–$C_8$alkyl, $C_3$–$C_6$-cycloalkyl, $C_2$–$C_4$alkenyl or $C_2$–$C_3$alkynyl; and $R_6$ is H or $C_1$–$C_6$alkyl.

3. A compound according to claim 1, of the formula I in which $R_1$ is $C_3$–$C_8$alkyl, $C_3$–$C_8$cycloalkyl, $C_3$–$C_8$alkenyl, $C_3$–$C_8$alkynyl, $C_3$–$C_8$alkoxy, $C_3$–$C_8$cycloalkoxy, $C_2$–$C_8$alkoxy-$C_1$–$C_4$alkyl, $C_1$–$C_8$alkoxy-$C_2$–$C_4$alkoxy-$C_1$–$C_4$alkyl, $C_1$–$C_8$alkoxy-$C_2$–$C_4$alkoxy, $C_4$–$C_8$cycloalkoxy-$C_1$–$C_3$alkyl, $C_3$–$C_8$alkenyloxy, $C_3$–$C_8$alkenyloxy-$C_1$–$C_3$alkyl, $C_3$–$C_8$alkynyloxy, $C_3$–$C_8$alkynyloxy-$C_1$–$C_3$alkyl, $C_3$–$C_8$haloalkyl, $C_3$–$C_8$haloalkenyl, $C_3$–$C_8$haloalkynyl, $C_3$–$C_8$haloalkoxy, $C_3$–$C_8$haloalkoxy, $C_1$–$C_3$alkyl, $C_3$–$C_8$haloalkenyloxy, $C_3$–$C_8$haloalkenyloxy-$C_1$–$C_3$alkyl, $C_3$–$C_8$haloalkynyloxy, $C_3$–$C_8$haloalkynyloxy-$C_1$–$C_3$alkyl, $C_3$–$C_8$alkylthio, $C_3$–$C_8$alkylthio-$C_1$–$C_3$alkyl, $C_2$–$C_8$alkylthio-$C_2$–$C_3$alkoxy, $C_2$–$C_8$alkylthio-$C_2$–$C_3$alkoxy-$C_1$–$C_4$alkyl, $C_2$–$C_8$alkylthio-$C_2$–$C_3$alkylthio, $C_2$–$C_8$alkylthio-$C_2$–$C_3$alkylthio-$C_1$–$C_4$alkyl, $C_2$–$C_8$alkoxy-$C_2$–$C_3$alkylthio or $C_2$–$C_8$alkoxy-$C_2$–$C_3$alkylthio-$C_1$–$C_4$alkyl;

$R_2$ is chlorine or bromine;

$R_3$ is H, halogen or methyl;

$R_4$ is H or methyl;

$R_5$ is H, $C_1$–$C_8$ alkyl, $C_3$–$C_6$cycloalkyl, $C_2$–$C_5$alkenyl or $C_2$–$C_5$alkynyl;

and $R_6$ is H or $C_1$–$C_6$alkyl.

4. A compound according to claim 1, of the formula I in which $R_1$ is $C_3$–$C_6$alkyl, $C_3$–$C_6$cycloalkyl, $C_3$–$C_6$alkenyl, $C_3$–$C_6$alkynyl, $C_3$–$C_8$alkoxy, $C_3$–$C_6$cycloalkoxy, $C_2$–$C_6$alkoxy-$C_1$–$C_4$alkyl, $C_1$–$C_6$alkoxy-$C_2$–$C_4$alkoxy, $C_4$–$C_6$cycloalkoxy-$C_1$–$C_3$alkyl, $C_3$–$C_6$alkenyloxy, $C_3$–$C_6$alkenyloxy-$C_1$–$C_3$alkyl, $C_3$–$C_6$alkynyloxy, $C_3$–$C_6$alkynyloxy-$C_1$–$C_3$alkyl, $C_3$–$C_6$haloalkyl, $C_3$–$C_6$haloalkenyl, $C_3$–$C_6$haloalkynyl, $C_3$–$C_6$haloalkoxy, $C_3$–$C_6$haloalkoxy-$C_1$–$C_3$alkyl, $C_3$–$C_6$haloalkenyloxy, $C_3$–$C_6$haloalkenyloxy-$C_1$–$C_3$alkyl, $C_3$–$C_6$haloalkynyloxy, $C_3$–$C_6$haloalkynyloxy-$C_1$–$C_3$alkyl, $C_3$–$C_6$alkylthio, $C_3$–$C_6$alkylthio-$C_1$–$C_3$alkyl, $C_2$–$C_6$alkylthio-$C_2$–$C_3$alkoxy or $C_2$–$C_6$alkylthio-$C_2$–$C_3$alkylthio;

$R_2$ is fluorine or chlorine;

$R_3$ is H, halogen or methyl;

$R_4$ is H or methyl;

$R_5$ is H, $C_1$–$C_8$alkyl, $C_3$–$C_6$cycloalkyl, $C_2$–$C_4$alkenyl or $C_2$–$C_3$alkynyl; and $R_6$ is H or $C_1$–$C_6$alkyl.

5. A compound according to claim 1, of the formula I in which $R_1$ is $C_4$–$C_6$alkyl, $C_4$–$C_6$cycloalkyl, $C_3$–$C_6$alkenyl, $C_3$–$C_5$alkynyl, $C_4$–$C_8$alkoxy, $C_5$–$C_6$cycloalkoxy, $C_2$–$C_4$alkoxy-$C_1$–$C_4$alkyl, $C_1$–$C_3$alkoxy-$C_2$–$C_4$alkoxy, $C_5$–$C_6$cycloalkoxy-$C_1$–$C_2$alkyl, $C_4$–$C_6$alkenyloxy, $C_3$–$C_6$alkenyloxy-$C_1$–$C_2$alkyl, $C_3$–$C_5$alkynyloxy, $C_3$–$C_5$alkynyloxy-$C_1$–$C_2$alkyl, $C_3$–$C_5$haloalkyl, $C_3$–$C_5$haloalkenyl, $C_3$–$C_6$haloalkynyl, $C_3$–$C_5$haloalkoxy, $C_3$–$C_5$haloalkoxy-$C_1$–$C_2$alkyl, $C_3$–$C_4$haloalkenyloxy, $C_3$–$C_4$haloalkenyloxy-$C_1$–$C_2$alkyl, $C_3$–$C_4$haloalkynyloxy, $C_3$–$C_4$haloalkynyloxy-$C_1$–$C_2$alkyl, $C_3$–$C_5$alkylthio, $C_3$–$C_5$alkylthio-$C_1$–$C_2$alkyl, $C_2$–$C_4$alkylthio-$C_2$–$C_3$alkoxy or $C_2$–$C_4$alkylthio-$C_2$–$C_3$alkylthio;

$R_2$ is chlorine or bromine;

$R_3$ is H, halogen or methyl;

$R_4$ is H or methyl;

$R_5$ is H, $C_1$–$C_8$alkyl, $C_3$–$C_6$cycloalkyl, $C_2$–$C_4$alkenyl, or $C_2$–$C_3$alkynyl; and $R_6$ is H or $C_1$–$C_3$alkyl.

6. A compound according to claim 1, of the formula I in which $R_1$ is $C_4$–$C_6$alkyl; cyclohexyl, $C_4$–$C_5$alkynyl, $C_4$–$C_5$alkoxy, $C_5$–$C_6$cycloalkoxy, $C_2$–$C_4$alkoxy-$C_1$–$C_4$alkyl, $C_1$–$C_2$alkoxyethoxy, $C_5$–$C_6$cycloalkoxymethyl, $C_4$–$C_6$alkenyloxy, $C_3$–$C_5$alkenyloxymethyl, $C_3$–$C_5$alkynyloxy, $C_3$–$C_4$haloalkoxy, $C_3$haloalkenyloxy, $C_3$haloalkenyloxymethyl, $C_3$haloalkynyloxy, $C_3$haloalkynyloxymethyl, $C_4$alkylthio, $C_4$alkylthiomethyl, $C_2$–$C_3$alkylthioethoxy or $C_2$–$C_3$alkylthioethylthio;

$R_2$ is chlorine, bromine or methyl;

$R_3$ is H, halogen or methyl;

$R_4$ is H or methyl;

$R_5$ is H, $C_1$–$C_8$alkyl, cyclopropyl, $C_2$–$C_4$alkenyl, or $C_2$–$C_3$alkynyl;

$R_6$ H or $C_1$–$C_3$alkyl.

7. A compound according to claim 1, of the formula I in which $R_1$ is sec-butoxy or isobutoxy;

$R_2$ is chlorine or bromine;

$R_3$ is H;

$R_4$ and $R_5$ are H; and $R_5$ is ethyl or propyl.

* * * * *